(12) United States Patent
Shelton, IV et al.

(10) Patent No.: US 11,627,961 B2
(45) Date of Patent: Apr. 18, 2023

(54) COMPRESSIBLE ADJUNCTS WITH DIFFERENT BEHAVIORAL ZONES

(71) Applicant: Cilag GmbH International, Zug (CH)

(72) Inventors: Frederick E. Shelton, IV, Hillsboro, OH (US); Jason L. Harris, Lebanon, OH (US); Michael J. Vendely, Lebanon, OH (US); Christopher Q. Seow, Cincinnati, OH (US)

(*) Notice: Subject to any disclaimer, the term of this patent is extended or adjusted under 35 U.S.C. 154(b) by 0 days.

(21) Appl. No.: 17/216,994

(22) Filed: Mar. 30, 2021

(65) Prior Publication Data
US 2022/0313248 A1 Oct. 6, 2022

(51) Int. Cl.
| | |
|---|---|
| *A61B 17/064* | (2006.01) |
| *A61B 17/068* | (2006.01) |
| *A61B 17/072* | (2006.01) |
| *A61B 17/00* | (2006.01) |

(52) U.S. Cl.
CPC .... *A61B 17/0686* (2013.01); *A61B 17/07292* (2013.01); *A61B 2017/00004* (2013.01); *A61B 2017/00893* (2013.01); *A61B 2017/07257* (2013.01); *A61B 2017/07271* (2013.01)

(58) Field of Classification Search
CPC .................. A61B 17/00004; A61B 17/07292
See application file for complete search history.

(56) References Cited

U.S. PATENT DOCUMENTS

| | | | |
|---|---|---|---|
| 5,833,695 A | 11/1998 | Yoon | |
| 7,143,925 B2 | 12/2006 | Shelton, IV et al. | |
| 7,601,118 B2 | 10/2009 | Smith et al. | |
| 8,062,330 B2 | 11/2011 | Prommersberger et al. | |
| 8,317,070 B2 | 11/2012 | Hueil et al. | |
| 8,393,514 B2 | 3/2013 | Shelton, IV et al. | |

(Continued)

FOREIGN PATENT DOCUMENTS

| | | |
|---|---|---|
| EP | 2113206 A2 | 11/2009 |
| EP | 2333701 A1 | 6/2011 |

(Continued)

OTHER PUBLICATIONS

International Patent Application No. PCT/IB2020/060710 entitled "Drug Delivery Device Sensing Modules", filed on Nov. 13, 2020, 100 pages.

(Continued)

*Primary Examiner* — Eyamindae C Jallow
(74) *Attorney, Agent, or Firm* — Mintz Levin Cohn Ferris Glovsky and Popeo, P.C.

(57) ABSTRACT

Compressible adjuncts for use with a staple cartridge are provided. In one exemplary embodiment, the compressible adjunct includes a non-fibrous adjunct material formed of at least one fused bioabsorbable polymer. The adjunct material is configured to be releasably retained on a staple cartridge and is configured to be delivered to tissue by deployment of staples in the cartridge The adjunct material includes a lattice macrostructure having at least one drug contained therein. The lattice macrostructure is formed of a plurality of unit cells, in which each unit cell is configured to eject a predetermined amount of drug from the adjunct material and the predetermined amount of the drug being a function of a compression profile of the respective unit cell.

19 Claims, 14 Drawing Sheets

(56) References Cited

U.S. PATENT DOCUMENTS

| | | | |
|---|---|---|---|
| 8,864,007 B2 | 10/2014 | Widenhouse et al. | |
| 9,084,602 B2 | 7/2015 | Gleiman | |
| 9,232,941 B2 | 1/2016 | Mandakolathur et al. | |
| 9,272,406 B2 | 3/2016 | Aronhalt et al. | |
| 9,282,962 B2 | 3/2016 | Schmid et al. | |
| 9,480,476 B2* | 11/2016 | Aldridge | A61B 17/072 |
| 9,681,936 B2 | 6/2017 | Hodgkinson et al. | |
| 9,913,642 B2 | 3/2018 | Leimbach et al. | |
| 9,999,408 B2 | 6/2018 | Boudreaux et al. | |
| 10,136,890 B2 | 11/2018 | Shelton, IV et al. | |
| 10,166,023 B2 | 1/2019 | Vendely et al. | |
| 10,172,611 B2 | 1/2019 | Shelton, IV et al. | |
| 10,172,617 B2 | 1/2019 | Shelton, IV et al. | |
| 10,172,618 B2 | 1/2019 | Shelton, IV et al. | |
| 10,258,332 B2 | 4/2019 | Schmid et al. | |
| 10,265,091 B2 | 4/2019 | Nativ et al. | |
| 10,349,939 B2 | 7/2019 | Shelton, IV et al. | |
| 10,368,869 B2 | 8/2019 | Olson et al. | |
| 10,433,846 B2 | 10/2019 | Vendely et al. | |
| 10,517,592 B2 | 12/2019 | Shelton, IV et al. | |
| 10,548,593 B2 | 2/2020 | Shelton, IV et al. | |
| 10,568,621 B2 | 2/2020 | Shelton, IV et al. | |
| 10,569,071 B2 | 2/2020 | Harris et al. | |
| 10,588,623 B2 | 3/2020 | Schmid et al. | |
| 10,772,732 B1 | 9/2020 | Miller et al. | |
| 10,939,911 B2 | 3/2021 | Huitema et al. | |
| 2002/0014951 A1 | 2/2002 | Kramer et al. | |
| 2004/0101546 A1 | 5/2004 | Gorman et al. | |
| 2004/0101548 A1 | 5/2004 | Pendharkar | |
| 2007/0021760 A1 | 1/2007 | Kelleher | |
| 2007/0034669 A1* | 2/2007 | de la Torre | A61B 17/07207 227/180.1 |
| 2007/0251835 A1 | 11/2007 | Mika et al. | |
| 2008/0051866 A1 | 2/2008 | Chen et al. | |
| 2009/0093550 A1 | 4/2009 | Rolfes et al. | |
| 2009/0123517 A1 | 5/2009 | Flanagan et al. | |
| 2009/0209031 A1 | 8/2009 | Stopek | |
| 2010/0331880 A1 | 12/2010 | Stopek | |
| 2012/0100200 A1 | 4/2012 | Belcheva et al. | |
| 2012/0241491 A1 | 9/2012 | Aldridge et al. | |
| 2013/0146643 A1 | 6/2013 | Schmid et al. | |
| 2013/0172929 A1 | 7/2013 | Hess et al. | |
| 2013/0221065 A1 | 8/2013 | Aronhalt et al. | |
| 2013/0256377 A1 | 10/2013 | Schmid et al. | |
| 2014/0205637 A1 | 7/2014 | Widenhouse et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0136831 A1 | 5/2015 | Baxter, III et al. | |
| 2015/0196296 A1 | 7/2015 | Swayze et al. | |
| 2015/0238191 A1 | 8/2015 | Schellin et al. | |
| 2015/0351761 A1 | 12/2015 | Shelton, IV et al. | |
| 2015/0351764 A1 | 12/2015 | Shelton, IV | |
| 2016/0100839 A1 | 4/2016 | Marczyk et al. | |
| 2016/0106427 A1 | 4/2016 | Shelton, IV et al. | |
| 2016/0345976 A1 | 12/2016 | González et al. | |
| 2017/0049448 A1 | 2/2017 | Widenhouse et al. | |
| 2017/0055986 A1 | 3/2017 | Harris et al. | |
| 2017/0055994 A1 | 3/2017 | Vendely et al. | |
| 2017/0056567 A1 | 3/2017 | Harris et al. | |
| 2017/0281181 A1 | 10/2017 | Matonick et al. | |
| 2017/0296213 A1 | 10/2017 | Swensgard et al. | |
| 2018/0085124 A1 | 3/2018 | Nativ et al. | |
| 2018/0235613 A1 | 8/2018 | Shelton, IV et al. | |
| 2018/0235625 A1* | 8/2018 | Shelton, IV | A61B 17/1155 |
| 2018/0353174 A1 | 12/2018 | Widenhouse et al. | |
| 2018/0353175 A1 | 12/2018 | Widenhouse et al. | |
| 2018/0353659 A1 | 12/2018 | Widenhouse et al. | |
| 2019/0200844 A1 | 7/2019 | Shelton, IV et al. | |
| 2019/0200981 A1 | 7/2019 | Harris et al. | |
| 2019/0201140 A1 | 7/2019 | Yates et al. | |
| 2019/0206004 A1 | 7/2019 | Shelton, IV et al. | |
| 2019/0206562 A1 | 7/2019 | Shelton, IV et al. | |
| 2019/0254654 A1 | 8/2019 | Shelton, IV et al. | |
| 2019/0254655 A1 | 8/2019 | Shelton, IV et al. | |
| 2019/0290267 A1 | 9/2019 | Baxter, III et al. | |
| 2019/0328390 A1 | 10/2019 | Harris et al. | |
| 2019/0344064 A1 | 11/2019 | Buchanan | |
| 2020/0205825 A1 | 7/2020 | Vendely et al. | |
| 2020/0238244 A1 | 7/2020 | Tchakalova et al. | |
| 2021/0077094 A1* | 3/2021 | Harris | A61B 17/07292 |
| 2021/0077109 A1* | 3/2021 | Harris | A61L 17/10 |
| 2021/0346015 A1 | 11/2021 | Krulevitch et al. | |
| 2022/0313145 A1 | 10/2022 | Shelton, IV et al. | |
| 2022/0313245 A1 | 10/2022 | Shelton, IV et al. | |
| 2022/0313246 A1 | 10/2022 | Shelton, IV et al. | |
| 2022/0313247 A1 | 10/2022 | Shelton, IV et al. | |
| 2022/0313255 A1 | 10/2022 | Shelton, IV et al. | |
| 2022/0313256 A1 | 10/2022 | Shelton, IV et al. | |
| 2022/0313257 A1 | 10/2022 | Shelton, IV et al. | |
| 2022/0313258 A1 | 10/2022 | Shelton, IV et al. | |
| 2022/0313259 A1 | 10/2022 | Shelton, IV et al. | |
| 2022/0313260 A1 | 10/2022 | Shelton, IV et al. | |
| 2022/0313261 A1 | 10/2022 | Shelton, IV et al. | |
| 2022/0313262 A1 | 10/2022 | Shelton, IV et al. | |
| 2022/0313874 A1 | 10/2022 | Shelton, IV et al. | |

FOREIGN PATENT DOCUMENTS

| | | |
|---|---|---|
| EP | 2395333 A1 | 12/2011 |
| EP | 2604196 A2 | 6/2013 |
| EP | 2628491 A2 | 8/2013 |
| EP | 3132811 A1 | 2/2017 |
| EP | 3162297 A1 | 5/2017 |
| EP | 3530199 A2 | 8/2019 |
| EP | 3756612 A2 | 12/2020 |
| EP | 3782558 A1 | 2/2021 |
| EP | 3791804 A2 | 3/2021 |
| EP | 3791809 A1 | 3/2021 |
| WO | 9824048 A1 | 6/1998 |
| WO | 2006044490 A2 | 4/2006 |
| WO | 2006068999 A2 | 6/2006 |
| WO | 2015187793 A1 | 12/2015 |
| WO | 2020021433 A1 | 1/2020 |
| WO | 2022079516 A1 | 4/2022 |

OTHER PUBLICATIONS

U.S. Appl. No. 17/022,520 entitled "Method of Applying Buttress to End Effector of Surgical Stapler", filed on Sep. 16, 2020, 226 pages.

U.S. Appl. No. 17/068,857 entitled "Adaptive Responses From Smart Packaging of Drug Delivery Absorbable Adjuncts", filed on Oct. 13, 2020, 97 pages.

Agren et al. (Jul. 2006) "Action of Matrix Metalloproteinases at Restricted Sites in Colon Anastomosis Repair: An Immunohistochemical and Biochemical Study", Surgery, 140(1):72-82.

Aslanian et al. (Mar.-Apr. 1984) "Dietary Intake and Urinary Excretion of Various Mineral Substances in Patients with Hypertension and Ischemic Heart Disease", Vopr Pitan, (2):16-9(English Abstract).

Bezwada Rao S. (2008) "Controlled Release of Drugs from Novel Absorbable Oligomers and Polymers", White Paper, Bezwada Biomedical, 7 pages.

Bezwada Rao S. (2008) "Functionalized Triclosan for Controlled Release Applications", White Paper, AP Bezwada Biomedical, 6 pages.

Bezwada Rao S. (2010) "Nitric Oxide and Drug Releasing Hydrolysable Macromers, Oligomers and Polymers", Chapter 11 of Biomaterials, ACS Symposium Series, American Chemical Society: Washington, DC, 24 pages.

Bezwada Rao S. (Mar. 2009) "Nitric Oxide and Drug Releasing Hydrolysable Macromers, Oligomers and Polymers", White Paper, Bezwada Biomedical, 9 pages.

Bosmans et al. (2015) "Colorectal Anastomotic Healing: Why the Biological Processes that Lead to Anastomotic Leakage Should Be Revealed Prior to Conducting Intervention Studies", BMC Gastroenterology, 15:180(6 pages).

(56) References Cited

OTHER PUBLICATIONS

Broughton et al. (Jun. 2006) "The Basic Science of Wound Healing", Plastic and Reconstructive Surgery, 117(7 Suppl):12S-34S.
Casalani et al. (Oct. 11, 2019) "A Perspective on Polylactic Acid-Based Polymers Use for Nanoparticles Synthesis and Applications", Frontiers in Bioengineering and Biotechnology, 7(259):1-16.
De Hingh et al. (Jun. 21, 2002) "The Matrix Metalloproteinase Inhibitor BB-94 Improves the Strength of Intestinal Anastomoses in the Rat", International Journal of Colorectal Disease, 17(5):348-354.
Fatouros et al. (Oct. 1999) "Influence of Growth Factors Erythropoietin and Granulocyte Macrophage Colony Stimulating Factor on Mechanical Strength and Healing of Colonic Anastomoses in Rats", The European Journal of Surgery, 165(10):986-992.
Gibson et al. (Nov. 2009) "MMPs Made Easy", Wounds International, 1(1):1-6.
Hayden et al. (Jun. 15, 2011) "The Role of Matrix Metalloproteinases in Intestinal Epithelial Wound Healing During Normal and Inflammatory States", Journal of Surgical Research, 168(2):315-324.
Holte et al. (Jun. 2009) "Cyclo-oxygenase 2 Inhibitors and the Risk of Anastomotic Leakage After Fast-Track Colonic Surgery", British Journal of Surgery, 96(6):650-654.
Kaemmer et al. (Oct. 2010) "Erythropoietin (EPO) Influences Colonic Anastomotic Healing in a Rat Model by Modulating Collagen Metabolism", Journal of Surgical Research, 163(2):e67-e72.
Kiyama et al. (Sep. 2002) "Tacrolimus Enhances Colon Anastomotic Healing in Rats", Wound Repair and Regeneration, 10(5):308-313.
Klein et al. (Jan. 2011) "Effect of Diclofenac on Cyclooxygenase-2 Levels and Early Breaking Strength of Experimental Colonic Anastomoses and Skin Incisions", European Surgical Research, 46(1):26-31.
Klein et al. (Jul. 18, 2010) "Physiology and Pathophysiology of Matrix Metalloproteases", Amino Acids, 41(2):271-290.
Krarup et al. (Apr. 26, 2013) "Expression and Inhibition of Matrix Metalloproteinase (MMP)-8, MMP-9 and MMP-12 in Early Colonic Anastomotic Repair", International Journal of Colorectal Disease, 28(8):1151-1159.
Martens et al. (Dec. 1991) "Postoperative changes in collagen synthesis in intestinal anastomoses of the rat: differences between small and large bowel", Gut, 32(12):1482-1487.
Moran et al. (May 15, 2007) "The Effect of Erythropoietin on Healing of Obstructive vs Nonobstructive Left Colonic Anastomosis: An Experimental Study", World Journal of Emergency Surgery, 2:13(6 pages).
Munireddy et al. (Dec. 2010) "Intra-abdominal Healing: Gastrointestinal Tract and Adhesions", Surgical Clinics of North America, 90(6):1227-1236(10 pages).
Øines et al. (Sep. 21, 2014) "Pharmacological Interventions for Improved Colonic Anastomotic Healing: A Meta-Analysis", World Journal of Gastroenterology, 20(35):12637-12648.
Raptis et al. (Mar. 2012) "The Effects of Tacrolimus on Colonic Anastomotic Healing in Rats", International Journal of Colorectal Disease, 27(3):299-308.
Savage et al. (Aug. 1997) "Role of Matrix Metalloproteinases in Healing of Colonic Anastomosis", Diseases of the Colon & Rectum, 40(8):962-970.
Siemonsma et al. (Mar. 1, 2003) "Doxycycline Improves Wound Strength After Intestinal Anastomosis in the Rat", Surgery, 133(3):268-276.
Thompson et al. (2006) "Clinical Review: Healing in Gastrointestinal Anastomoses, Part I", Microsurgery, 26(3):131-136.
Vandenbroucke et al. (Dec. 2014) "Is There New Hope for Therapeutic Matrix Metalloproteinase Inhibition?", Nature Reviews Drug Discovery, 13(12):904-927.
Witte et al. (Aug. 2003) "Repair of Full-thickness Bowel Injury", Critical Care Medicine, 31(8 Suppl):S538-S546.
U.S. Appl. No. 17/217,252, filed Mar 30, 2021, Method for Treating Tissue.
U.S. Appl. No. 17/216,977, filed Mar 30, 2021, Compressible Adjuncts With Fluid Control Features.
U.S. Appl. No. 17/216,978, filed Mar 30, 2021, Compressible Adjuncts With Drug Release Features.
U.S. Appl. No. 17/216,982, filed Mar 30, 2021, Compressible Adjuncts With Drug Release Features.
U.S. Appl. No. 17/216,985, filed Mar 30, 2021, Compressible Adjuncts With Drug Dosage Control Features.
U.S. Appl. No. 17/216,914, filed Mar 30, 2021, Smart Packaging for Tissue Adjuncts.
U.S. Appl. No. 17/216,946, filed Mar 30, 2021, Passively Powered Packaging for Tissue Adjuncts.
U.S. Appl. No. 17/216,953, filed Mar 30, 2021, Using Smart Packaging in Adjusting Use of Tissue Adjuncts.
U.S. Appl. No. 17/216,960, filed Mar 30, 2021, Monitoring Healing After Tissue Adjunct Implantation.
U.S. Appl. No. 17/217,578, filed Mar 30, 2021, Implantable Adjuncts Having Adjustable Degradation Profile.
U.S. Appl. No. 17/217,680, filed Mar 30, 2021, Compressible Adjuncts With Healing-Dependent Degradation Profile.
U.S. Appl. No. 17/217,736, filed Mar 30, 2021, Tissue Thickness Compensating Adjuncts Having Regions of Differential Expansion.
U.S. Appl. No. 17/217,784, filed Mar 30, 2021, Composite Adjuncts That Degrade Through Multiple Different Mechanisms.
(2022) What are Stents?, NIH National Heart, Lung, and Blood Institute, 3 pages.
Miaurus et al. (2004) "Bioabsorbable Implant Material Review", Operative Techniques in Sports Medicine, 12:158-160.
International Search Report and Written Opinion received for PCT Application No. PCT/IB2022/052798, dated Aug. 18, 2022, 14 pages.
International Search Report and Written Opinion received for PCT Application No. PCT/IB2022/052804, dated Jul. 8, 2022, 16 pages.
International Search Report and Written Opinion received for PCT Application No. PCT/IB2022/052806, dated Jul. 27, 2022, 17 pages.
International Search Report and Written Opinion received for PCT Application No. PCT/IB2022/052807, dated Jul. 7, 2022, 14 pages.
International Search Report and Written Opinion received for PCT Application No. PCT/IB2022/052809, dated Jul. 27, 2022, 17 pages.
International Search Report and Written Opinion received for PCT Application No. PCT/IB2022/052811, dated Jul. 7, 2022, 18 pages.
International Search Report and Written Opinion received for PCT Application No. PCT/IB2022/052813, dated Jul. 27, 2022, 15 pages.
International Search Report and Written Opinion received for PCT Application No. PCT/IB2022/052815, dated Jul. 20, 2022, 13 pages.
International Search Report and Written Opinion received for PCT Application No. PCT/IB2022/052816, dated Jul. 12, 2022, 16 pages.
International Search Report and Written Opinion received for PCT Application No. PCT/IB2022/052818, dated Aug. 10, 2022, 14 pages.
Invitation to Pay Additional Fees received for PCT Application No. PCT/IB2022/052795, dated Jul. 20, 2022, 11 pages.
Invitation to Pay Additional Fees received for PCT Application No. PCT/IB2022/052796, dated Jul. 27, 2022, 13 pages.
Invitation to Pay Additional Fees received for PCT Application No. PCT/IB2022/052822, dated Aug. 12, 2022, 13 pages.

* cited by examiner

COMPRESSIBLE ADJUNCTS WITH DIFFERENT BEHAVIORAL ZONES

FIELD OF THE INVENTION

The present disclosure relates generally to compressible adjuncts and methods of using compressible adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling.

Various implantable materials have been developed for use in combination with stapling tissue, however there remains a need for improved materials that address some of the aforementioned problems.

SUMMARY

Compressible adjuncts for use with a staple cartridge are provided. In one exemplary embodiment, the compressible adjunct includes a non-fibrous adjunct material formed of at least one fused bioabsorbable polymer. The adjunct material is configured to be releasably retained on a staple cartridge and is configured to be delivered to tissue by deployment of staples in the cartridge The adjunct material includes a lattice macrostructure having at least one drug contained therein. The lattice macrostructure is formed of a plurality of unit cells, in which each unit cell is configured to eject a predetermined amount of drug from the adjunct material and the predetermined amount of the drug being a function of a compression profile of the respective unit cell.

The plurality of unit cells can have a variety of configurations. In some embodiments, at least one unit cell of the plurality of unit cells can have a variable wall thickness. In some embodiments, the plurality of unit cells can include first unit cells and second unit cells. The first unit cells can have a first compression profile and the second unit cells can have a second compression profile that is different than the first compression profile. In some embodiments, each unit cell can have a plurality of compression zones. The plurality of compression zones can include a first compression zone and a second compression zone. The first compression zone can have a first compressive strength and the second compression zone can have a second compressive strength that is different than the first compressive strength. The first compression zone can configured to compress from a first uncompressed height to a first compressed height. The second compression zone can be configured to compress from a second uncompressed height to a second compressed height that is different than the first compressed height.

In some embodiments, each unit cell can include a plurality of sub-structures formed therein. The plurality of sub-structures can be configured to control the deformation behavior of the respective unit cell when the adjunct material is being compressed. The plurality of sub-structures can include first sub-structures and second sub-structures. The first sub-structures can be projections that extend inward from a wall of the unit cell and the second sub-structures can be recesses formed in a wall of the unit cell. In certain embodiments, the plurality of sub-structures can include at least one internal stopping member.

In some embodiments, the plurality of unit cells can include Schwarz-P structures. In such embodiments, the lattice macrostructure can comprise a plurality of connecting structures. The plurality of connecting structures can extend between and connect adjacent Schwarz-P structures to each other.

In another embodiment, a compressible adjunct for use with a staple cartridge includes a non-fibrous adjunct material formed of at least one fused bioabsorbable polymer. The adjunct material is configured to be releasably retained on a staple cartridge and is configured to be delivered to tissue by deployment of staples in the cartridge. The adjunct material includes a lattice main structure having at least one drug contained therein. The lattice main structure can include first sub-structures formed in at least one first portion of the lattice main structure and second sub-structures formed in at least one second portion of the lattice main structure. The first sub-structures and the second sub-structures are configured to control a first release rate and a second release rate, respectively, of the at least one drug from the adjunct material when the adjunct material is compressed and in a tissue deployed state, the first release rate being different than the second release rate.

The first and second portions of the lattice main structure can have a variety of configurations. In some embodiments, the first portion of the lattice main structure can have a first wall thickness and the second portion of the lattice main structure can have a second wall thickness that is different than the first wall thickness. In certain embodiments, the first portion of the lattice main structure can be configured to deform from a first undeformed state to a first deformed state. In such embodiments, the second portion of the lattice main structure can be configured to deform from a second undeformed state to a second deformed state that is different than the first deformed state.

The first sub-structures and the second sub-structures can have a variety of configurations. In some embodiments, the first sub-structures can include at least one of a first projection that extends inward from a wall of the lattice main structure and a first recess formed in a wall of the lattice main structure. In some embodiments, the second sub-structures can include at least one of a second projection that extends inward from a wall of the lattice main structure and a second recess formed in a wall of the lattice main structure.

In certain embodiments, at least one of the first sub-structures and the second sub-structures can include at least one internal stopping member.

The lattice main structure can have a variety of configurations. In some embodiments, the lattice main structure can include a plurality of Schwarz-P structures. In such embodiments, the lattice main structure can include a plurality of connecting structures. The connecting structures can extend between and connect adjacent Schwarz-P structures to each other.

BRIEF DESCRIPTION OF THE DRAWINGS

This invention will be more fully understood from the following detailed description taken in conjunction with the accompanying drawings, in which.

DETAILED DESCRIPTION

Figure 1:
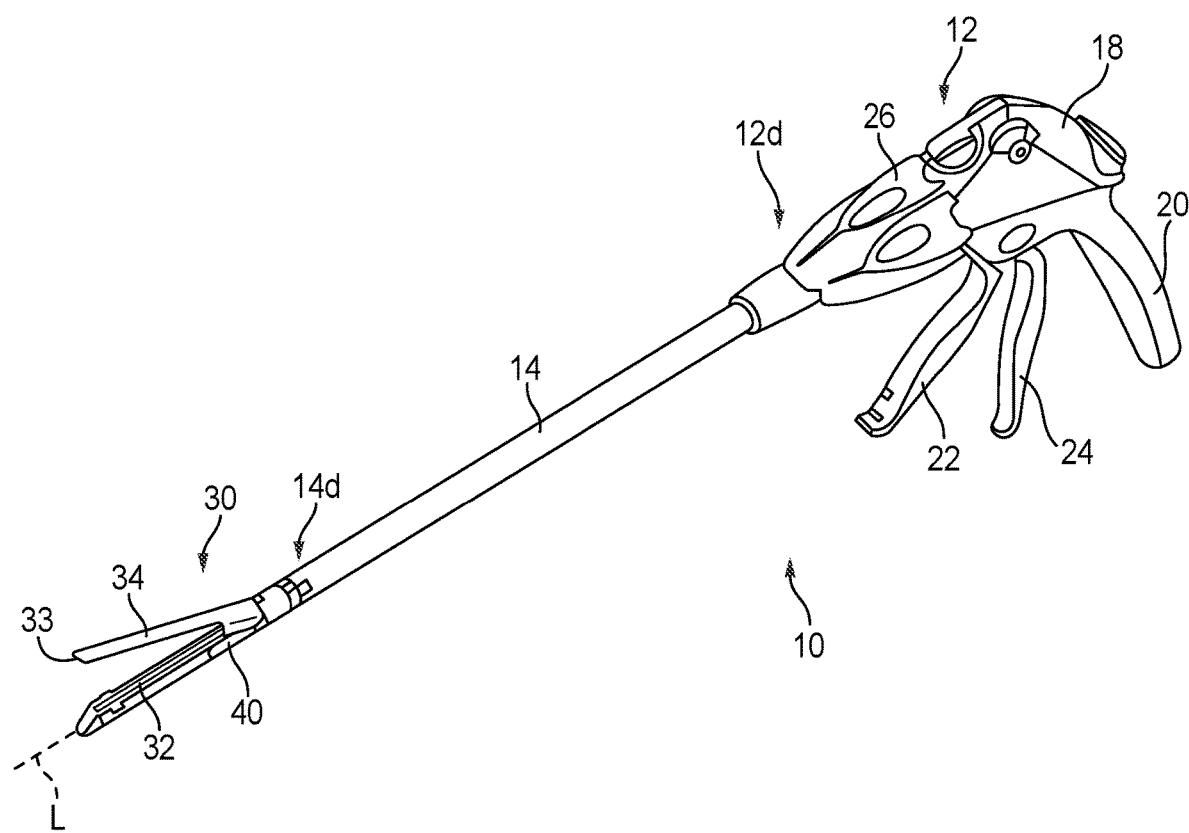
FIG. 1 is a perspective view of one exemplary embodiment of a conventional surgical stapling and severing instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, referred to herein as "adjuncts," in conjunction with surgical instruments to help improve surgical procedures. "Adjuncts" are also referred to herein as "adjunct materials." While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing, and/or is experiencing another tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissue's movement around these puncture sites can minimize the size the holes may grow to under tension. In some instances, the adjunct(s) can be configured to wick or absorb beneficial fluids, e.g., sealants, blood, glues, and the like, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts.

In other embodiments, the adjunct(s) can be used with surgical instruments that are configured to seal tissue without using staples (e.g., by using energy, such as RF or ultrasound), for example, as described in U.S. Pat. No. 10,172,611, which is incorporated by reference herein in its entirety.

In some instances, the adjunct(s) can be configured to compensate for variations in tissue thickness when the adjunct(s) are stapled to tissue. In such instances, the adjunct can be also be referred to as a "tissue thickness compensator." A tissue thickness compensator has an uncompressed (undeformed), or pre-deployed, height that is greater than the height of a staple that is in a formed configuration. Additional details on exemplary tissue thickness compensators can be found in, for example, U.S. Pat. No. 8,864,007, which is incorporated by reference herein in its entirety. A tissue thickness compensator can be attached and released from a staple cartridge in a variety of ways, for example, as described in U.S. Pat. Nos. 9,272,406, and 10,136,890, each of which is incorporated by reference herein in its entirety.

In addition to the disclosures herein, additional details pertaining to the adjunct(s) and other exemplary adjuncts can be found in, for example, U.S. Pat. Nos. 10,172,611 and 10,433,846 and U.S. patent application Ser. No. 17/009,769, filed on Sep. 1, 2020, and entitled "Compressible Non-Fibrous Adjuncts," each of which is incorporated herein by reference in its entirety.

Alternatively or in addition, the adjunct(s) can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Alternatively or in addition, the adjunct(s) can have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc. In addition to the disclosures herein, additional details on drug eluting adjuncts can be found in U.S. Pat. Nos. 9,232,941 and 10,569,071, each of which is incorporated herein by reference in its entirety.

Surgical Stapling Instruments

A variety of surgical instruments can be used in conjunction with the adjunct(s) and/or medicant(s) disclosed herein. The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
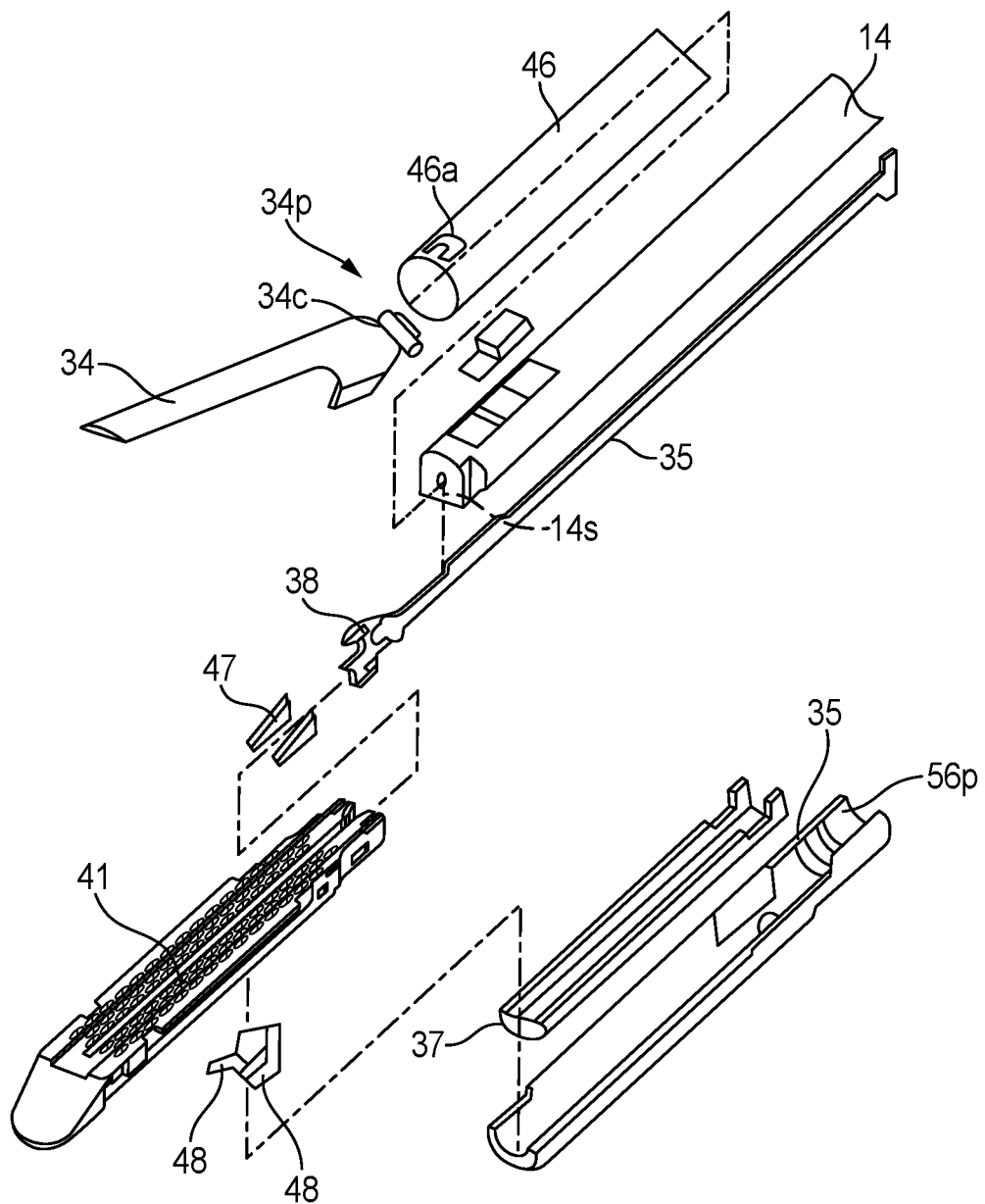
FIG. 2 is a top view of a staple cartridge for use with the surgical stapling and severing instrument of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
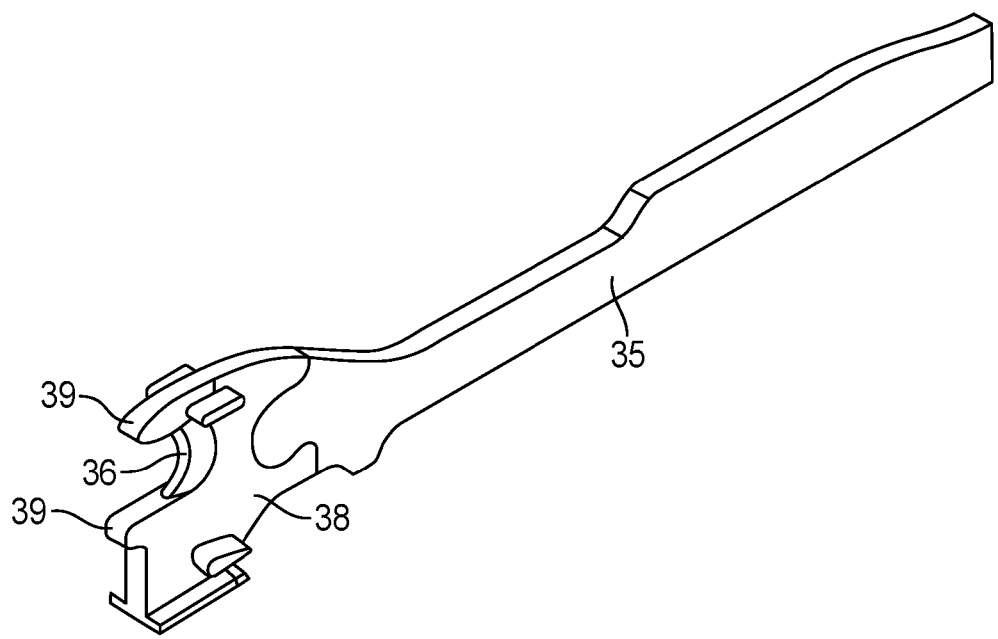
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
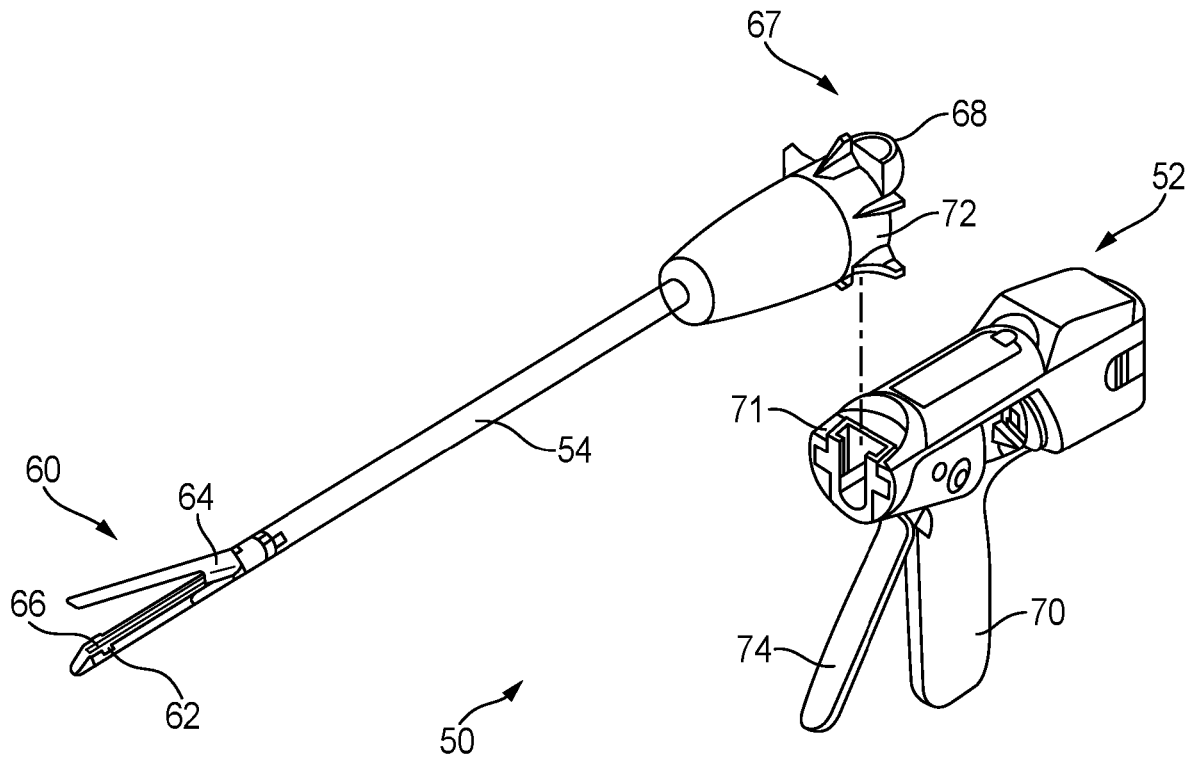
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
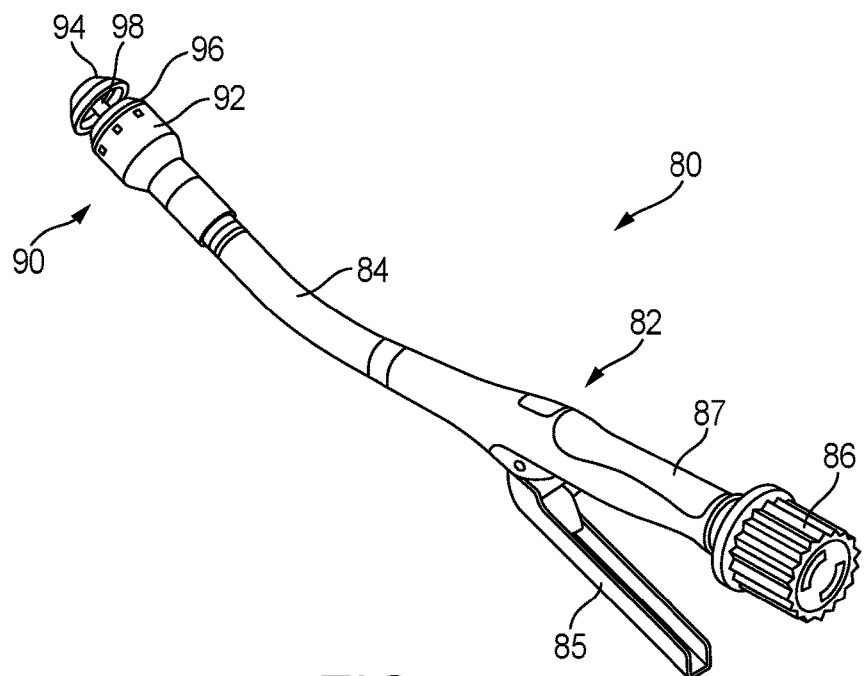
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, e.g., move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

Implantable Adjuncts

Figure 6:
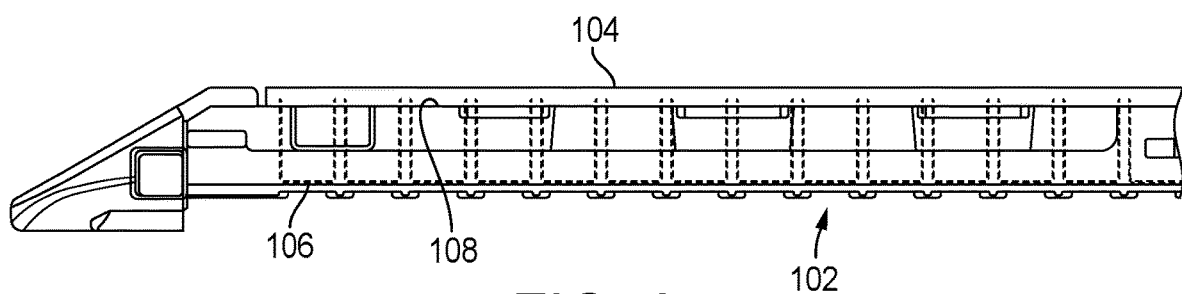
FIG. 6 is a longitudinal cross-sectional view of an exemplary embodiment of a staple cartridge having an exemplary adjunct attached to a top or deck surface thereof.

As indicated above, various implantable adjuncts are provided for use in conjunction with surgical stapling instruments. When used in conjunction with a surgical stapler, the adjunct(s) can be disposed between and/or on jaws of the stapler, incorporated into a staple cartridge disposed in the jaws, or otherwise placed in proximity to the staples. For example, as shown in FIG. 6, an adjunct 104 is positioned against a staple cartridge 102. For sake of simplicity, the adjunct 104 is generally illustrated in FIG. 6, and various structural configurations of the adjunct are described in more detail below. While partially obstructed in FIG. 6, the staple cartridge 102 includes staples 106 that are configured to be deployed into tissue. The staples 106 can have any suitable unformed (pre-deployed) height. For example, the staples 106 can have an unformed height between about 2 mm and 4.8 mm. Prior to deployment, the crowns of the staples can be supported by staple drivers (not shown).

In the illustrated embodiment, the adjunct 104 can be releasably mated to at least a portion of the top surface or deck surface 108 of the staple cartridge 102. In some embodiments, the top surface 108 of the staple cartridge 102 can include one or more surface features. Alternatively, or in addition, one or more adhesives can be used to releasably mate the adjunct to the staple cartridge 102. The one or more surface features and/or the one or more adhesives can be configured to engage the adjunct 104 to avoid undesirable movements of the adjunct 104 relative to the staple cartridge 102 and/or to prevent premature release of the adjunct 104 from the staple cartridge 102. Exemplary surface features are described in U.S. Patent Publication No. 2016/0106427, which is incorporated by reference herein in its entirety. Additional details on adhesives for temporary attachment to instruments and other exemplary adhesives can be found in U.S. Pat. Nos. 9,282,962, 10,172,617, 10,172,618, 10,258, 332, 10,517,592, 10,548,593, 10,568,621, and 10,588,623, each of which is incorporated by reference herein in its entirety. Additional details on attachment methods and other exemplary methods can be found in U.S. Pat. Nos. 10,166, 023 and 10,349,939 and U.S. patent application Ser. No. 17/022,520, filed on Sep. 16, 2020, and entitled "Method of Applying Buttress to End Effector of Surgical Stapler," each of which is incorporated by reference herein in its entirety.

Figure 7:
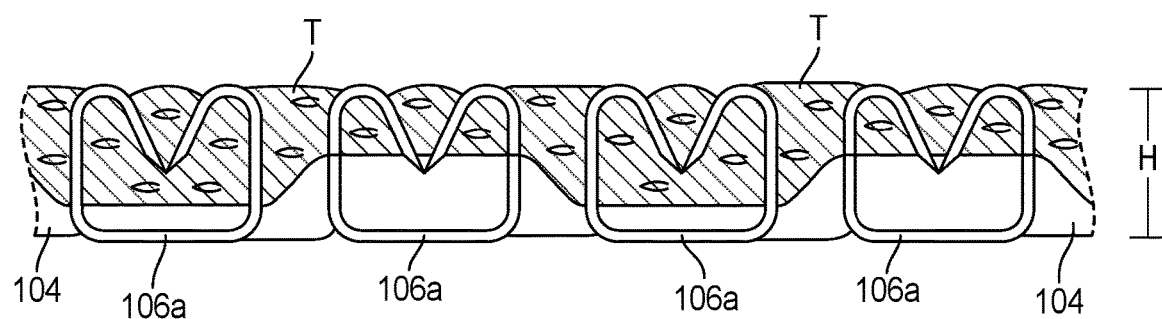
FIG. 7 is a partial-schematic illustrating the adjunct of FIG. 6 in a tissue deployed condition.

In certain instances, the adjunct can be compressible to permit the adjunct to compress to varying heights to thereby compensate for different tissue thickness that are captured within a deployed staple. For example, as illustrated in FIG. 6, the adjunct 104 has an uncompressed (undeformed), or pre-deployed, height and is configured to deform to one of a plurality of compressed (deformed), or deployed, heights. As such, the adjunct 104 can have an uncompressed height which is greater than the fired height of the staples 106 disposed within the staple cartridge 102 (e.g., the height (H) of the fired staple 106a in FIG. 7). That is, the adjunct 104 can have an undeformed state in which a maximum height of the adjunct 104 is greater than a maximum height of a fired staple (e.g., a staple that is in a formed configuration). In such instances, the adjunct can be referred to as a "tissue thickness compensator." In one embodiment, the uncompressed height of the adjunct 104 can be about 10% taller, about 20% taller, about 30% taller, about 40% taller, about 50% taller, about 60% taller, about 70% taller, about 80% taller, about 90% taller, or about 100% taller than the fired height of the staples 106. In certain embodiments, the uncompressed height of the adjunct 104 can be over 100% taller than the fired height of the staples 106, for example.

The adjuncts can have a variety of configurations, and can be formed from various materials. In general, an adjunct can be formed from one or more of a film, a foam, an injection molded thermoplastic, a vacuum thermoformed material, a fibrous structure, an additive manufacturing material, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010, which is incorporated by reference herein in its entirety.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

In other embodiments, the adjunct can be formed using a 3D printing process(es) compatible with absorbable polymers. Non-limiting examples of suitable 3D printing processes include stereolithography (SLA or SL), material jetting, selective laser sintering (SLS), and fused filament fabrication as understood by a person skilled in the art.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA) (e.g., Dexon and Neoveil), poly(lactic-co-glycolic acid) (PLGA), polycaprolactone (PCL), polyglycolide (PGL), trimethylene carbonate (TMC), polylactic acid (PLA) (e.g., Linvatec Bioscrew and Bionx Implants Smart Screw), poly(trimethylene carbonate (PTMC), polyethylene diglycolate (PEDG), poly(propylene fumarate) (PPF), polyethylene ether (PEE), poly(ethylene glycol) (PEG), poly(N-isopropylacrylamide, poly(amino acid), poly(epoxycarbonate), poly(2-oxypropylene carbonate), poly(diol citrates), polymethacrylate anhydrides, poly(ethoxyethylene diglycolate), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides (e.g., REVA ReZolve Stents), and tyrosine-based polyesteramides (e.g., TYRX). The copolymers can also include poly(lactic acid-co-polycaprolactone) (PLA/PCL) (e.g., 16-18 month hydrolyzed), poly (L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), LPLA/DLPLA (e.g., Optima), PLGA-PCL (e.g., 15:85 (PCL: 50% D,L-Lactide: 50% Glycolide), 40:60 (PCL: 50% D,L-Lactide: 50% Glycolide), and 40:60 (PCL: 85% D,L-Lactide: 15% Glycolide), PLGA-PCL-PLGA, and PLGA-PEG-PLGA.

An adjunct can also include special polymer terminations, including (meth)acrylate and organically-derived polymers. Non-limiting examples of organically-derived polymers include those derived from collagen (e.g., Avitene, Endoavitene, Instat, Integran, Veritas, and Microfibrillar Collagen (MFC)).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, NeoRecormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids agents that inhibit mitosis and microtubule formation (e.g., Vinblastine, Vincristine, Vindesine, Vinorelbine), angiostatic inhibiting agents that inhibit cell growths or cell expansion (e.g., Axitinib (Inlyta), Bevacizumab (Avastin), Cabozantinib (Cometriq), Everolimus (Afinitor, Zortress) Lenalidomide (Revlimid), Pazopanib (Votrient), Ramucirumab (Cyramza), Regorafenib (Stivarga), Sorafenib (Nexavar), Sunitinib (Sutent), Thalidomide (Synovir, Thalomid), Vandetanib (Caprelsa), Zib-aflibercept (Zaltrap), antiangiogenic polysaccharide, aplidine (dehydrodidemnin B), sapogenins viz. 20(S)-protopanaxadiol, and 20(S)-protopanaxatriol), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Exemplary medicants also include agents that encourage blood supply regeneration following coronary artery disease (CAD) (e.g., $VEGF_{165}$ protein, $AdVEGF_{165}$, $AdVEGF_{121}$, and $VEGF_{165}$ plasmid) or periphery artery disease (PAD) (e.g., $VEGF_{165}$ plasmid, $AdVEGF_{121}$, SB-509 (SFP-VEGF plasmid), $AdVEGF_{165}$, and Ad2-HIF1α-VP16 (WALK trial)).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Drug Release Features

In certain embodiments, the adjuncts can have configurations designed to control drug movement though and out of the adjuncts when the adjuncts are in a tissue deployed state (e.g., stapled to tissue in vivo). As discussed below, the adjuncts can include active drug release features that are designed to effect drug release from the adjuncts in a controlled and tailored manner when such features are activated (e.g., thermal and/or mechanical activation). That is, unless activated, the active drug release features are configured to encapsulate the drug and therefore inhibit drug from being released from the adjunct. In this way, the active drug release features can help prevent premature drug release from the adjuncts.

The adjuncts can generally be formed at least one fused bioabsorbable polymer that is configured to be releasably retained on a staple cartridge and that is configured to be delivered to tissue by deployment of staples in the cartridge. In an exemplary embodiment, the adjunct material can include a lattice macrostructure having drug delivery microstructures formed in the lattice macrostructure, and each drug delivery microstructure can have drug disposed therein. The drug delivery microstructures can be configured to encapsulate the drug to thereby prevent drug release until the plurality of drug delivery microstructures are thermally ruptured in response to changes in body temperature and/or mechanically ruptured in response to at least one of clamping, stapling, and cutting of the adjunct material (e.g., mechanical failure). In certain embodiments, the drug delivery microstructures can have an internal cavity (e.g., microreservoir) defined therein. As used herein, the term "lattice macrostructure" is used synonymously with the term "lattice main structure."

In order to enable formation of macro and micro structures, the adjuncts can be non-fibrous adjuncts. Unlike conventional adjuncts (e.g., adjuncts that are not three-dimensionally printed, such as foam adjuncts and woven/non-woven fibrous adjuncts), the non-fibrous adjuncts are three-dimensionally (3D) printed and therefore can be formed with microstructures (units) that are consistent and reproducible. That is, unlike with other methods of manufacture, 3D printing significantly improves control over microstructural features such as placement and connection of elements. As a result, variability in both the microstructure(s) and attendant properties of the present adjuncts is decreased, as compared to conventional adjuncts. Further, 3D printing can create adjuncts with microstructural features that could not otherwise be formed or generated within conventional adjuncts. The present non-fibrous adjuncts can also be adapted for use with a variety of staples and tissue types.

In certain embodiments, the drug delivery microstructures can be thermally ruptured in response to a variety temperature related events (e.g., a temperature increase or decrease). In some embodiments, the drug delivery microstructures can be configured to thermally rupture in response to an increase in temperature.

The increase in temperature can be in response to an infection of the stapled tissue. That is, once the adjunct is in a tissue deployed state (e.g., stapled to tissue in vivo), the temperature at or proximate to the stapled adjunct can increase due to infected tissue (e.g., due to swelling and/or localized increased in blood flow). As a result, this increase in temperature can initiate the release of the drug from one or more of the drug delivery microstructures. For example, in some embodiments, the drug delivery microstructures can in the form of microcontainers that are sealed with a material that is configured to break down or liquefy at an elevated body temperature (e.g., greater than about 37° C.). Once the microcontainers are unsealed, the drug can be released out of the adjunct, and in certain embodiments, the drug (e.g., antibiotic(s)) can be used to treat the infection. In certain embodiments, the microcontainers are sealed with a plug that is formed of the material. Alternatively, or in addition, where the initial release of the drug one or more drug delivery microstructures are already thermally ruptured, the temperature increase can be used to accelerate the release of the drug from the drug delivery microstructures.

In some embodiments, the drug delivery microstructures can be configured to thermally rupture when the adjunct material is at or above an activation temperature. The activation temperature can be associated with body temperature (e.g., about 37° C.). As a result, the body temperature can be used as a gating key that can initiate the release of the drug from one or more of the drug delivery microstructures. For example, in some embodiments, the drug delivery microstructures can be in the form of microcontainers that are sealed with a material that is configured to break down or liquefy when exposed to body temperature and/or in the presence of humidity. In certain embodiments, the microcontainers can be sealed with a plug that is formed of the material. In other embodiments, the drug delivery microstructures can be formed of a structure (e.g., formed of a shape memory material) having initially sealed pores, and once the adjunct is in a tissue deployed state, the exposure to body temperature can cause the sealed pores to open and release drug therefrom.

In some embodiments, daily temperature variation at or proximate to the stapled tissue can be used to control the rate of drug release from the drug delivery microstructures. For example, a combination of time and temperature dependent release features could allow the administration of drug to the patient over multiple days at approximately the same time. In one embodiment, temperature activated release feature(s) can be encapsulated in different thicknesses of time dependent release materials. In another embodiment, the drug delivery microstructures can be in the form of microcontainers that are sealed with a different material(s) or material thicknesses that are configured to release at body temperature. These microcontainers can be sealed with plugs having different thicknesses and/or formed of different materials relative to each other. In one embodiment, first microcontainers can be sealed with first plugs and second microcontainers can be sealed with second plugs that differ from the first plugs in material and/or thickness.

In other embodiments, the drug delivery microstructures can be mechanically ruptured in response to clamping, stapling, and/or cutting the adjunct (e.g., mechanical failure). For example, in use, once the adjunct is releasably retained to a staple cartridge of a surgical end effector, the clamping of the adjunct between opposing jaws of the end effector (e.g., first jaw (e.g., anvil) compression of the adjunct, prior to trocar introduction, or first compression with tissue between the jaws) can cause at least a portion of the drug delivery microstructures to rupture (e.g., shear, fracture, or otherwise open). Once ruptured, drug that was otherwise encapsulated within these drug delivery microstructures can then be released. The encapsulated drug can be in a variety of forms, for example, in an inter-powder form (e.g., dry or freeze dried), a polymer interaction form (e.g., pendent molecule on a polymer strand), or liquid form (e.g., a liquid that is does interact with the base polymer of the adjunct (e.g., oil based for a hydrolyses polymer or water based in an enzyme degradable polymer). Alternatively, or in addition, once the adjunct is releasably retained on the cartridge, any drug delivery microstructures that overlap with the staples disposed within the cartridge can be punctured during stapling of the adjunct. As a result, drug release from the overlapping drug delivery microstructures can be effected by staple advancement through the adjunct. Alternatively, or in addition, once the adjunct is releasably retained on the cartridge, any drug delivery microstructures that overlap with a slot of the cartridge that is configured to receive a cutting element can be severed by the cutting element as it advances through the slot during cutting of the adjunct. As a result, drug release from the overlapping drug delivery microstructures can be effected by advancement of a cutting element through the adjunct.

Drug can be incorporated into the adjuncts in a variety of ways and at different times. In some embodiments, drug can be incorporated into an adjunct prior the adjunct being releasably retained on the staple cartridge and/or anvil. In other embodiments, drug can be incorporated into an adjunct after the adjunct is releasably retained on the staple cartridge and/or anvil adjuncts. For example, in one embodiment, once an adjunct is applied to the staple cartridge and/or anvil (e.g., via an adjunct applicator), a user can clamp onto a drug delivery device (e.g., a sponge containing the drug, e.g., a drug in the form of a liquid, that is removably coupled to the adjunct) to apply at least one drug to the adjunct. In another embodiments, the drug delivery device can be a 3D printed bottle or container having at least one drug disposed therein. The 3D printed container can be attached to the adjunct and configured to delivery drug to the adjunct upon compression of the 3D printed container (e.g., squeezing). In certain embodiments, the 3D printed container is attached to the adjunct and remains attached when the adjunct is stapled to tissue. In one embodiment, the 3D printed container includes a one-way valve that retains at least one drug within the 3D printed container and only allows the at least one drug to exit when the 3D printed container is compressed. Alternatively, or in addition, the 3D printed container can include a cap that is configured to be cut off by a cutting element as the cutting element advances through the staple cartridge. Alternatively, or in addition, compression of the 3D printed container can be effected by swelling of the tissue that is stapled to the adjunct during healing or during an infection.

The drug delivery microstructures can have a variety of configurations. In certain embodiments, the drug delivery microstructures can be strut-based unit cells characterized by the presence of sharp corners or angles, non-strut-based unit cells characterized by curved surface, or a combination thereof. With non-strut based unit cells, the unit cells, for example, can be based on triply periodic minimal surfaces (TPMS). TPMS is a minimal surface that repeats itself in three dimensions. The term "minimal surface" as used in this description refers to a minimal surface as known in mathematics. As such, in some embodiments, the unit cell can be a triply periodic minimal surface structure (e.g., Schwarz-P, Schwarz Diamond, and the like) having passageways extending therethrough. For example, the non-strut based unit cells can be a hollow structure. Additional details on triply periodic minimal surface structures, such as Schwarz-P structures can be found in previously mentioned U.S. patent application Ser. No. 17/009,740, filed Sep. 1, 2020, and entitled "Compressible Non-Fibrous Adjuncts," which is incorporated herein by reference in its entirety. In certain embodiments, the lattice main structure can include a combination of strut-based unit cells (e.g., hollow struts) and non-strut based unit cells (e.g., one or more triply periodic minimal surface structures). In one embodiment, the non-strut based unit cells are interconnected to each other via connecting structures. These connecting structures can take the form of hollow tubes or struts. In certain embodiments, the unit cell(s) can include the connecting structures.

Each exemplary adjunct as described below is illustrated in partial form (e.g., not in full-length), and therefore a person skilled in the art will appreciate that the adjunct can be longer in length, e.g., along its longitudinal axis (LA) as identified in each embodiment. The length can vary based on a length of the staple cartridge or anvil. The width can also vary as needed. Further, each exemplary adjunct is configured to be positioned atop a cartridge or anvil surface such that the longitudinal axis L of each adjunct is aligned with and extends along the longitudinal axis (LA) of the cartridge or anvil. These adjuncts are structured so as to compress when exposed to compressive forces (e.g., stress or load).

Figure 8:
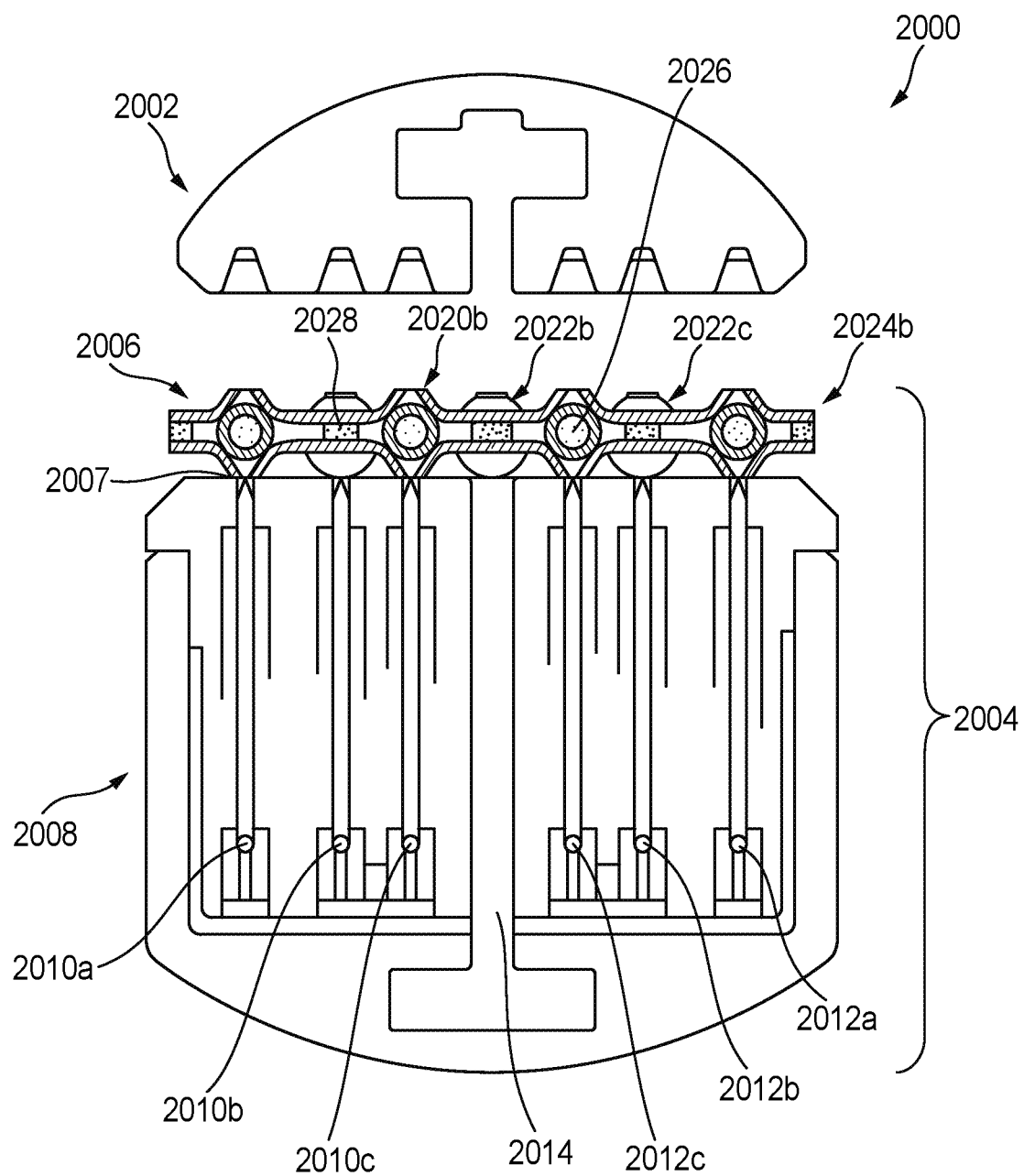
FIG. 8 is a cross-sectional front view of an exemplary embodiment of a surgical end effector having an anvil and a stapling assembly, the stapling assembly having an exemplary embodiment of an adjunct releasably retained on a staple cartridge, showing the surgical end effector in a closed positioned without tissue positioned between the anvil and the stapling assembly.
Figure 9:
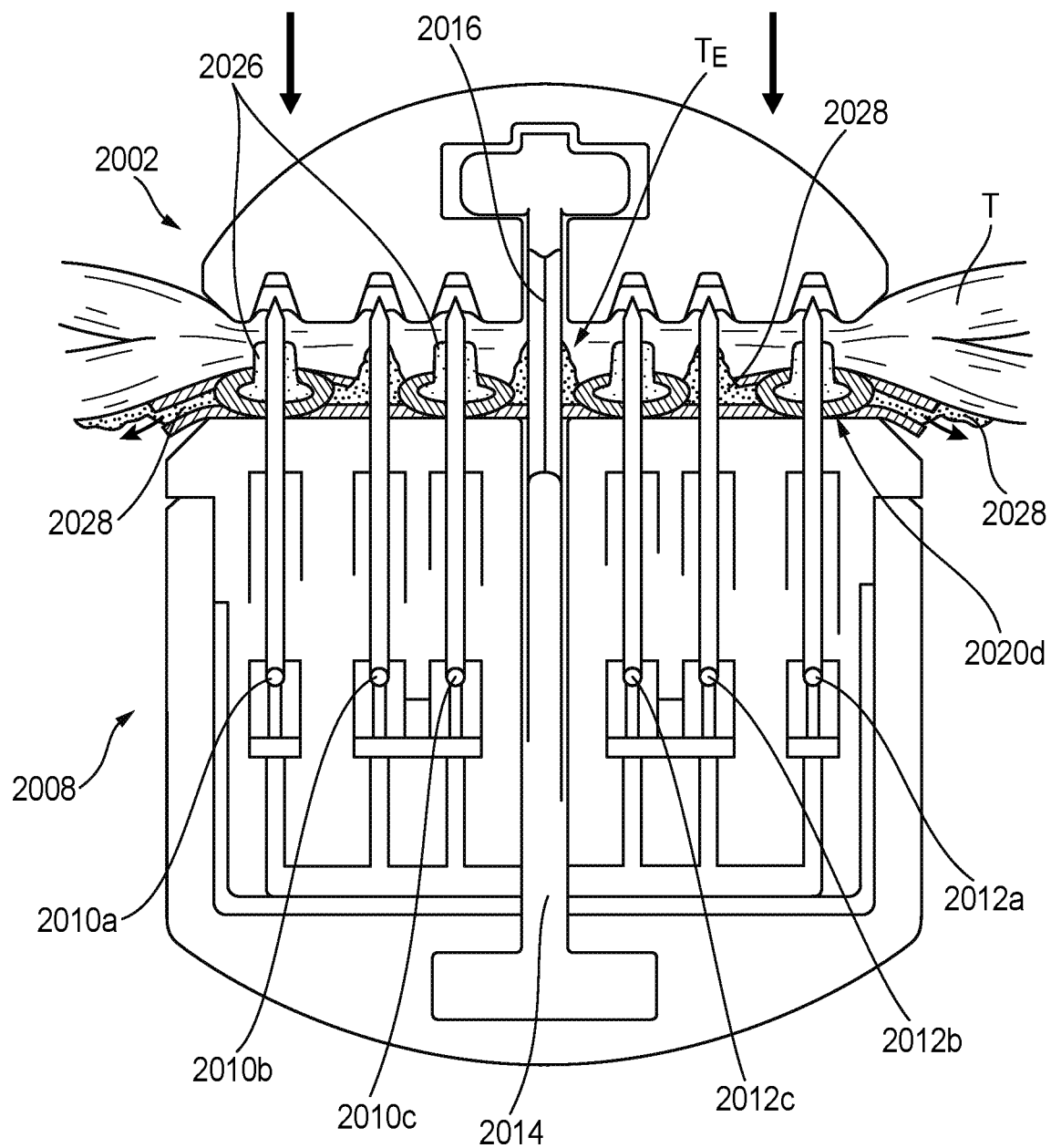
FIG. 9 is a cross-sectional front view of the surgical end effector of FIG. 8, showing tissue clamped between the anvil and the stapling assembly and the tissue being stapled to the compressible non-fibrous adjunct.

FIG. 8 and FIG. 9 illustrate an exemplary embodiment of a surgical end effector 2000 having an anvil 2002 and a stapling assembly 2004. The stapling assembly 2004 includes an adjunct 2006 releasably retained on a top or deck surface 2007 of a staple cartridge 2008 (e.g., the cartridge surface that faces the anvil). The cartridge 2008 has two sets of three rows of staples (only three staples 2010a, 2010b, 2010c, 2012a, 2012b, 2012c from each set are illustrated) that are disposed within the staple cartridge 2008, and a slot 2014 defined within the staple cartridge 2008 that is configured to receive a cutting element 2016 (see FIG. 9). FIG. 8 illustrates the surgical end effector 2000, and thus the anvil 2002, in a fully closed position, whereas FIG. 9 illustrates tissue T being clamped between the anvil 2002 and stapling assembly 2004, being stapled to the adjunct 2006 via staples 2010a, 2010b, 2010c, 2012a, 2012b, 2012c, and the tissue T and the adjunct 2006 being cut via cutting element 2016. While not illustrated, the anvil 2002 is pivotally coupled to an elongate staple channel and the stapling assembly 2004 is positioned within and coupled to elongate staple channel.

Figure 10:
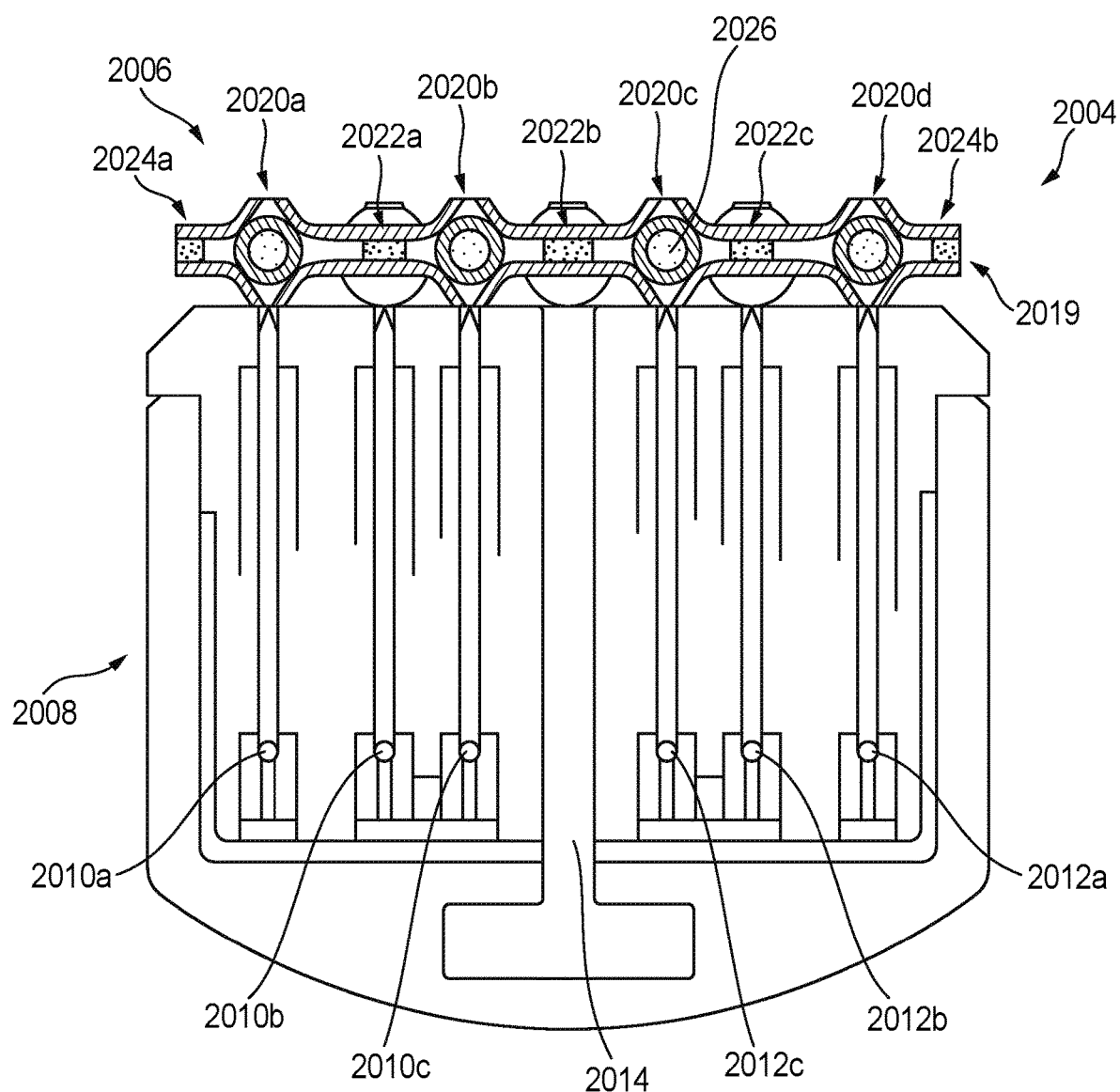
FIG. 10 is a cross-sectional front view of only the stapling assembly of FIG. 8.

While the adjunct 2006 can have a variety of configurations, as shown in FIG. 8, and in more detail in FIG. 10, the adjunct 2006 has a lattice macrostructure 2019 with drug delivery microstructures formed therein (only nine drug delivery microstructures 2020a, 2020b, 2020c, 2020d, 2022a, 2022b, 2022c, 2024a, 2024b are shown). While the drug delivery microstructures 2020a, 2020b, 2020c, 2020d, 2022a, 2022b, 2022c, 2024a, 2024b can have a variety of configurations, in this illustrated embodiment, lattice macrostructure 2019 includes first drug delivery microstructures 2020a, 2020b, 2020c, 2020d, each having a first drug 2026 disposed therein, and second drug delivery microstructures 2022a, 2022b, 2022c, 2024a, 2024b, each having a second drug 2028 disposed therein. The first and second drug delivery microstructures 2020a, 2020b, 2020c, 2020d, 2022a, 2022b, 2022c, 2024a, 2024b are each configured to encapsulate the respective first and second drugs 2026, 2028 therein (FIG. 8 and FIG. 10 until the first and second drug delivery microstructures 2020a, 2020b, 2020c, 2020d, 2022a, 2022b, 2022c, 2024a, 2024b are mechanically ruptured (FIG. 9). In some embodiments, the first drug and second drug can be different, whereas in other embodiments, the first drug and second drug can be the same. Further, in embodiments where the first and second drugs are different, one portion of the first drug delivery microstructures and/or second drug delivery microstructures can include the first drug and another portion of the first drug delivery microstructures and/or second drug delivery microstructures can include the second drug.

The first and second drug delivery microstructures 2020a, 2020b, 2020c, 2020d, 2022a, 2022b, 2022c, 2024a, 2024b can have a variety of configurations. In this illustrated embodiment, the first drug delivery microstructures 2020a, 2020b, 2020c, 2020d are in the form of hollow unit cells each with an internal cavity (e.g., a microreservoir) defined therein. The second drug delivery microstructures are in the form of internal hollow tubes (drug delivery microstructures 2022a, 2022b, 2022c) and external hollow tubes (drug delivery microstructures 2024a, 2024b) each having an internal cavity (e.g., a microreservoir). The internal hollow tubes 2022a, 2022b, 2022c extend between and connect adjacent hollow unit cells to each other, whereas the external hollow tubes 2024a, 2024b extend outward from the outer-most hollow unit cells (drug delivery microstructures 2020a, 2020d). As a result, the hollow unit cells (drug delivery microstructures 2020a, 2020b, 2020c, 2020d) are in fluid communication with each other such that a continuous network of pathways are present within the adjunct 2006. A person skilled the art will appreciate that the structural configuration and number of the first and second drug delivery microstructures can depend at least upon the size and shape of lattice macrostructure and the structural configuration of the staple cartridge the adjunct is to be releasably retained thereto, and therefore, the adjunct is not limited to the structure and number of drug delivery microstructures illustrated in the figures. Further, while two different drug delivery microstructures are illustrated, in other embodiments, the lattice macrostructure can include any suitable type and number of drug delivery microstructures.

The first and second drug delivery microstructures 2020a, 2020b, 2020c, 2020d, 2022a, 2022b, 2022c, 2024a, 2024b can be positioned within different regions of the adjunct 2006 such that drug release from the microstructures can be effected by different activation mechanism (e.g., clamping, stapling, and/or cutting of the adjunct). In this illustrated embodiment, the first drug delivery microstructures 2020a, 2020b, 2020c, 2020d are positioned at regions of the adjunct 2006 that overlap with the inner and outer staple rows 2010a, 2010c, 2012a, 2012c of the staple cartridge 2008. More specifically, the outer-most hollow unit cells (first drug delivery microstructures 2020a, 2020d) overlap with outer-most staple rows 2010a, 2012a, respectively, and the inner-most hollow unit cells (first drug delivery microstructure 2020b, 2020c) overlap with inner-most staple rows 2010c, 2012c, respectively. Further, the outer-most internal hollow tubes (second drug delivery microstructures 2022a, 2022c) overlap with intermediate staple rows 2010b, 2012b, respectively. As a result, as shown in FIG. 9, as the staples 2010a, 2010b, 2010c, 2012a, 2012b, 2012c advance through the respective overlapping drug delivery microstructures 2020a, 2020b, 2020c, 2020d, 2022a, 2022b, 2022c, the staples puncture, and thus cause mechanical rupture of these drug delivery microstructures. As such, drug can then be released from these drug delivery microstructures 2020a, 2020b, 2020c, 2020d, 2022a, 2022b, 2022c and into the tissue (e.g., at or around the staples holes created within the tissue) as shown in FIG. 9. Further, the clamping of the adjunct 2006 between the anvil 2002 and the staple cartridge 2008 during staple deployment can help facilitate drug release from the punctured drug delivery microstructures 2022a, 2022b, 2020c, 2020d, 2022a, 2022b, 2022c.

As further shown in FIG. 8 and FIG. 10, the inner-most internal hollow tube (drug delivery microstructure 2022b) is positioned within the region of the adjunct 2006 that overlaps with the slot 2014 of the staple cartridge 2008. As a result, in use, as shown in FIG. 9, as the cutting element 2016 advances through the slot 2014, the overlapping drug delivery microstructure 2022b is severed, and thus mechanically ruptured. As such, drug can then be released from drug delivery microstructure 2022b and into the tissue (e.g., along the severed edges $T_E$ of the tissue T) as shown in FIG. 9.

Further, in this illustrated embodiment, the external hollow tubes (drug delivery microstructures 2024a, 2024b) are positioned within the outer-most regions of the adjunct and therefore are adjacent to the outer-most staple rows 2010a, 2012a. As a result, in use, as shown in FIG. 9, when the adjunct 2006 and tissue T are clamped between the anvil 2002 and the staple cartridge 2008, the resulting force applied to the adjunct 2006 can thereby cause drug disposed within the external hollow tubes (drug delivery microstructures 2024a, 2024b) to be released therefrom and into the tissue T. A person skilled in the art will appreciate that in other embodiments, clamping of the adjunct can by itself cause mechanical rupture of any of the drug delivery microstructures within the adjunct.

In some embodiments, the adjunct can include drug release features that can be configured to control the dosage release of the drug from the adjunct when the adjunct is in a tissue deployed state. For example, in certain embodiments, the drug release features can be configured to effect a metered drug dosage over time while the adjunct is in a tissue deployed state. In other embodiments, the drug release features can be configured to effect a variable drug dosage over time while the adjunct is in a tissue deployed state. For example, the drug release features can allow for an initial bolus dosage of drug, followed by subsequent metered dosages of drug (e.g., based on a timeframe relative to expected healing profiles of the tissue that is stapled to the adjunct). Alternatively, or in addition, the adjunct can include one or more materials (e.g., hydrogels) that are positioned within passageways formed the adjunct. These materials can serve as a type of drug release feature(s) that is configured to inhibit drug movement through the respective passageways for a predetermined period of time.

For example, in one exemplary embodiment, the adjunct can be formed of at least one fused bioabsorbable polymer and can have a lattice macrostructure having primary and secondary microreservoirs formed in the lattice macrostructure. The primary microreservoirs and secondary microreservoirs differ in size relative to each other and can contain drug disposed therein. The primary microreservoirs can be configured to release drug therefrom upon activation and the secondary microreservoirs can be configured to release drug therefrom upon degradation of at least one of the at least one fused bioabsorbable polymer so that the combination of the primary and secondary microreservoirs control the dosage of drug being released from the adjunct when the adjunct is in a tissue deployed state. As such, the primary microreservoirs can serve as active drug release features and the secondary microreservoirs can serve as passive drug release features.

Activation (e.g., mechanical failure) of the primary microreservoirs can occur in a variety ways. For example, the primary reservoirs can be configured to be punctured (e.g., by stapling the adjunct as discussed above), fractured (e.g., by clamping the adjunct as discussed above), severed (e.g., by cutting the adjunct ad discussed above), or any combination thereof.

In certain embodiments, the lattice macrostructure can include at least one internal stopping member formed in each primary microreservoir. The at least one internal stopping member can be configured to limit the amount of deformation of the respective primary microreservoir when the adjunct material is being compressed. In some embodiments, the at least one internal stopping member can be configured to degrade over time while the adjunct material is in a tissue deployed state to thereby allow for greater deformation of the respective primary microreservoir when the adjunct material is being compressed. In certain embodiments, the primary microreservoirs can be formed of a first fused bioabsorbable polymer and the at least one internal stopping member can be formed of a second fused bioabsorbable polymer that degrades faster that the first fused bioabsorbable polymer.

Depending on the form of drug disposed within the primary microreservoirs, the primary microreservoirs can be sealed, or otherwise capped off. For example, in embodiments where the drug is in a liquid form, the primary microreservoir can be sealed so as to prevent the drug from premature release from the adjunct. The primary microreservoir can be sealed in any suitable manner (e.g., the seal can be 3D printed or jetted/extruded/rolled into place (BAM)). In embodiments where the drug is in a powered form, the primary microreservoir can be unsealed, or otherwise open. Further, in certain embodiments, the primary microreservoirs can be unsealed when the drug is in a vicious liquid form.

The primary and secondary microreservoirs can each be defined by respective microstructures that are formed within the lattice macrostructure. In some embodiments, the primary microreservoirs can be defined by respective hollow unit cells or hollow tubes. That is, the internal cavity of a hollow unit cell or hollow tube can serve as a primary microreservoir. In some embodiments, the secondary microreservoirs can be voids or openings that are defined within a wall of the lattice macrostructure.

Figure 11:
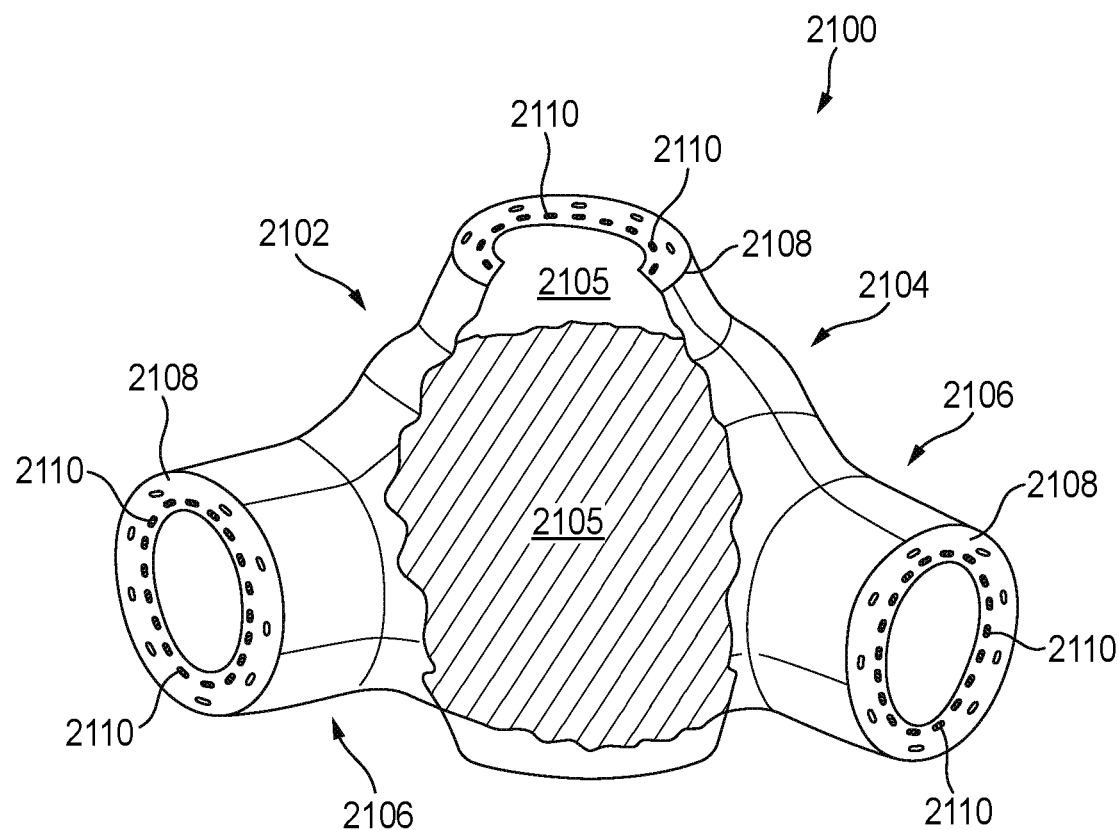
FIG. 11 is a partial cut-away perspective view of a portion of another embodiment of an adjunct.

FIG. 11 illustrates another embodiment of an adjunct 2100 having a lattice macrostructure 2102 that is formed of unit cells 2104 (e.g., Schwarz-P structures) that connected to each other via connecting structures 2106. For sake of simplicity, only one unit cell 2104 and a portion of two connecting structures 2106 are being illustrated. While the unit cell 2104 and two connecting structures 2106 can have a variety of configurations, in this illustrated embodiment, the unit cell 2104 is a hollow structure with an internal cavity 2105 defined therein and the two connecting structures 2106 are each a hollow tube. As a result, the unit cells 2104 are in fluid communication with each other such that a continuous network of pathways can be present or formed within the adjunct 2100.

As shown, a first drug (depicted as hatch markings) is disposed within the internal cavity 2105 (e.g., a primary microreservoir) of the unit cell 2104. The unit cell 2104 can be configured to encapsulate the first drug within its internal cavity 2105 until the unit cell is activated. Thus, in use, once the unit cell 2104 is activated, (e.g., compressed from an uncompressed state to a compressed state or is ruptured in response to at least one of clamping, stapling, and cutting of the adjunct 2100), the first drug can be released therefrom and into tissue.

As further shown in FIG. 11, voids 2010 (e.g., secondary microreservoirs) are defined within the walls 2108 of the lattice macrostructure 2102. Each void 2010 has a second drug disposed therein, and each void 2010 is configured to release the second drug therefrom in response to at least partial degradation or erosion of the defining portion of the respective wall 2108. Stated differently, each void 2010 is configured to encapsulate the second drug to thereby prevent drug release therefrom until structural degradation of at least a portion of the defining wall 2108. As a result, the combination of the internal cavities 2105 (e.g., primary microreservoirs) of the unit cells 2104 and the voids 2010 (e.g., secondary microreservoirs) within the walls 2108 of the lattice macrostructure 2102 can control the dosage of drug that is released from the adjunct 2100 when the adjunct 2100 is in a tissue deployed state.

While the internal cavities 2105 (e.g., primary microreservoirs) and the voids 2110 (e.g., secondary microreservoirs)

can have a variety of shapes and sizes, as shown, the internal cavities 2105 are larger in size, and thus have larger drug loading capacity, compared to that of the voids 2110. This can allow for a large bolus of the first drug to be released upon activation of the unit cells 2104, followed by smaller doses of the second drug to be released upon structural degradation of the walls 2108 of the lattice macrostructure 2102.

Further, while not illustrated, the adjunct 2100 can include at least one internal stopping member (e.g., like internal stopping members 2314, 2316 shown in FIG. 14) formed within the unit cells 2104. The at least one internal stopping member can be configured to limit the amount of deformation of the respective unit cells when the adjunct is being compressed. For example, in some embodiments, with the at least one internal stopping member in place, each activation of the unit cell can eject a smaller bolus of the first drug. In other embodiments, the at least one internal stopping member can be configured to degrade over time while the adjunct is in a tissue deployed state. As a result, during one or more subsequent activations of the unit cell, this degradation can allow a greater amount of drug to be released (e.g., compared to the amount(s) of drug prior to degradation). In other words, as degradation progresses, drug release can increase. Thus, the bolus of drug released from the adjunct 2100 can vary in response to changes in the geometry of the unit cells during activation. In certain embodiments, the adjunct 2100 can include one or more hydrogels (e.g., disposed within one or more passageways of the adjunct) that can function to inhibit flow therethrough for a predetermined period of time.

In certain embodiments, the adjunct can include first and second voids (e.g., secondary microreservoirs) that are positioned within different regions of the walls of the lattice macrostructure. For example, FIG. 12 illustrates a portion of a connector of a unit cell of an adjunct 2200 that is similar to the adjunct 2100 in FIG. 11, except that the adjunct 2200 includes first voids 2202 with a first drug 2204 disposed therein and second voids 2206 with a second drug 2208 disposed therein.

Figure 12:
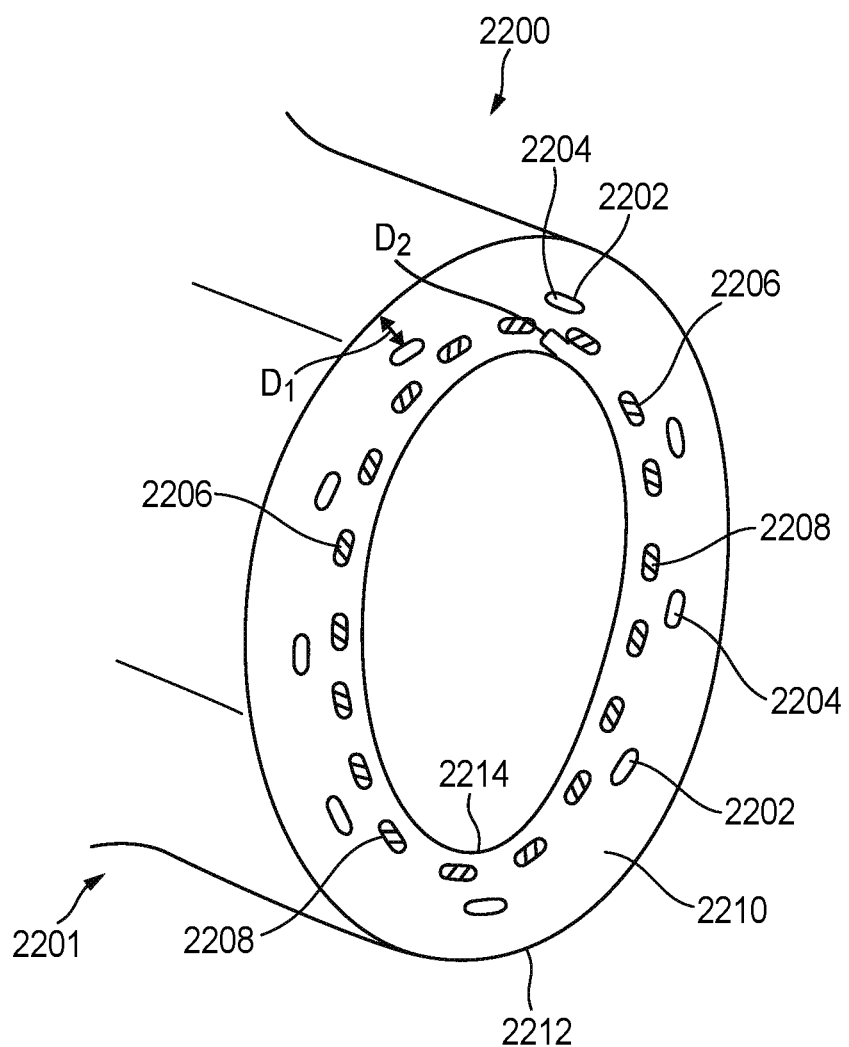
FIG. 12 is a magnified cross-sectional side view of another embodiment of an adjunct, showing the adjunct in an initial state (t=0)
Figure 13:
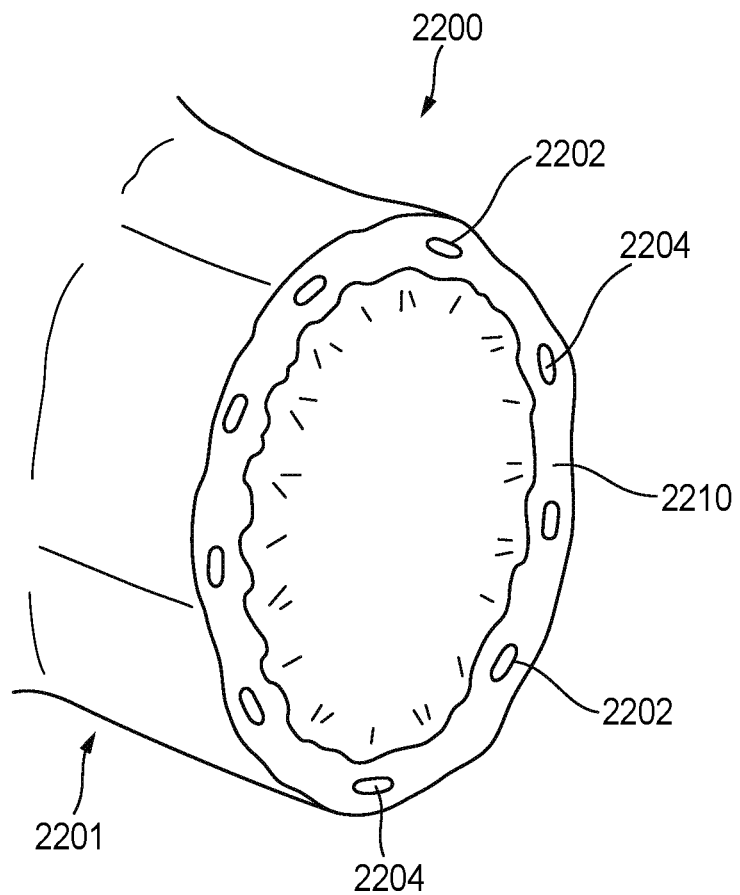
FIG. 13 is the adjunct of FIG. 12, showing the adjunct in a partially degraded state (t>0)

As shown in FIG. 12, the first voids 2202 are positioned proximate to the outer surface 2212 of the wall 2210, and the second voids 2206 are positioned proximate to the inner surface 2214 of the wall 2210. In this illustrated embodiment, the first voids 2202 (e.g., outer voids) encircle the second voids 2206 (e.g., inner voids). Further, as shown, the distance $D_1$ between the first voids 2202 and the outer surface 2212 of the wall 2210 is greater than the distance D2 between the second voids 2206 and the inner surface 2214 of the wall 2210. As a result, as shown in FIG. 13, as the wall 2210 degrades the second drug 2208 is released from the adjunct 2100 prior to the first drug. That is, drug release from the first and second voids 2202, 2206 can therefore be a function of their respective position within the wall(s) 2210 (e.g., relative to the inner or outer wall surface). In some embodiments, the first and second drugs can be the same with a metered release from the adjunct. In other embodiments, the first and second drugs can be different so as to fulfill different needs based on different time periods or events while the adjunct is stapled to tissue (e.g., time periods relative to expected healing profiles of the stapled tissue that).

Figure 14:
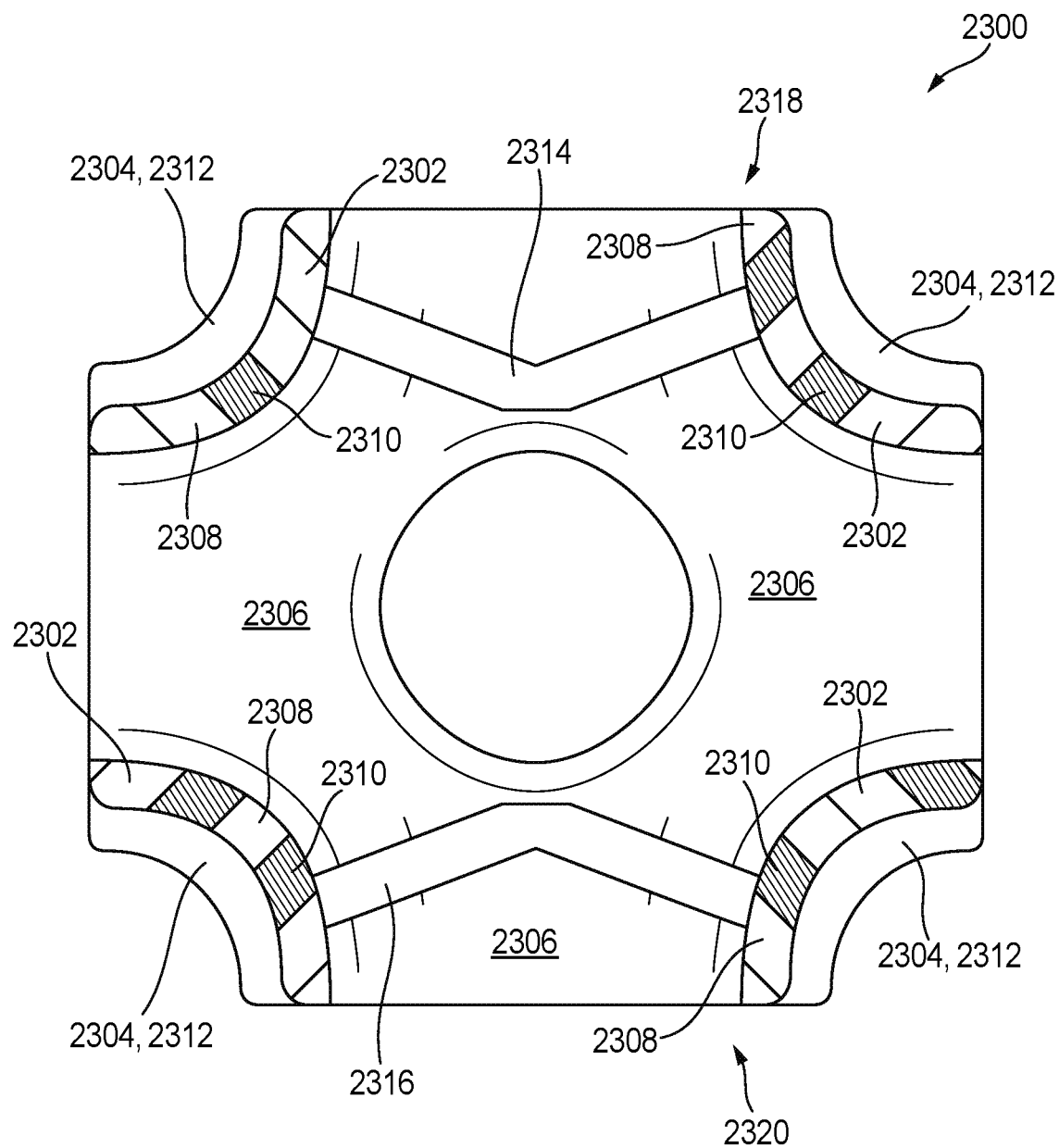
FIG. 14 is cross-sectional view of an exemplary embodiment of a multi-layered unit cell.

In some embodiments, the adjunct can be formed from multi-layered unit cells such that drug dosage can vary in response to polymer erosion of one or more layers of the unit cell. For example, FIG. 14 illustrates an exemplary embodiment of a multi-layered unit cell 2300 that can be used to form any adjunct described herein. While the unit cell 2300 can have a variety of configurations, in this illustrated embodiment, the unit cell 2300 is a Schwarz-P structure having an inner layer 2302 and an outer layer 2304. As shown, the illustrated Schwarz-P structure is a hollow in which the inner layer 2302 defines an internal cavity 2306 of the Schwarz-P structure.

The inner layer 2302 and the outer layer 2304 can be formed of a variety of materials. The inner layer 2302 can formed of a blend of a first fused bioabsorbable polymer 2308 and drug 2310. In some embodiments, as shown in FIG. 14, drug 2310 can be discretely embedded within portions of the inner layer 2302. In other embodiments, the drug can be homogenously dispersed throughout the first fused bioabsorbable polymer. In either embodiment, the first fused bioabsorbable polymer 2308 can be configured to undergo degradation when the adjunct is stapled to tissue so as to release discrete amounts of the drug into the internal cavities 2305 of the unit cells 2300 over time.

The outer layer 2304 can be formed of a second fused bioabsorbable polymer 2312 that is different than the first fused bioabsorbable polymer 2308. In some embodiments, the second fused bioabsorbable polymer 2312 can be configured to degrade at a degradation rate that is less than a degradation rate of the first fused bioabsorbable polymer 2308. In such embodiments, the outer layer 2304 can maintain the structural integrity of the overall unit cell 2300 while the inner layer 2302 degrades. As a result, the unit cell 2300 can function as a pump when the adjunct is being compressed. That is, when a force is applied to the adjunct, the unit cell 2300 can be configured to deform or compress so as to drive at least a portion of the drug that is present in the internal cavity 2306 (e.g., due to erosion of at least a portion of the inner layer 2302) out of the adjunct and to adjacent tissue when the adjunct is in a tissue deployed state.

As further shown in FIG. 14, the unit cell 2300 can include internal stopping members 2314, 2316 that are formed therein and that extend into the internal cavity 2306. These internal stopping members 2314, 2316 are configured to contact each other when the unit cell 2300 is being compressed to limit the amount of deformation of the unit cell 2300. While the unit cell 2300 can include any number of internal stopping members, in this illustrated embodiment, the unit cell 2300 includes one set of internal stopping members 2314, 2316.

The internal stopping members 2314, 2316 can have a variety of configurations. Further, the internal stopping members can have the same or different structural configurations. As shown in FIG. 14, the one set of members include first and second opposing stopping members 2314, 2316, each having a V-shaped configuration in which the first stopping member 2314 is positioned proximate to a top portion 2318 of the unit cell 2300 and the second stopping member 2316 is positioned proximate to a bottom portion 2320 of the unit cell 2300. A person skilled in the art will appreciate that the number and structural configurations of the internal stopping members depend at least upon the structural configuration and size of the unit cell, and therefore, in other embodiments, a unit cell can have a different number of internal stopping members and/or internal stopping members having other suitable shapes and sizes.

In other embodiments, adjuncts are provided having microstructures (units) with sub-structures formed in the microstructures to thereby create differing zones exhibiting different mechanical behavior within the adjuncts when the adjuncts are in a tissue deployed state. For example, the interconnections or geometries of the microstructures can have pre-defined bend zones, flexion shapes, deflection stops, elongation zones, or other variable geometry to thereby encourage a first portion of the adjunct to move or deform differently than other portion(s). The structural configuration of the microstructures can therefore be tailored to have respective compression profiles that control the flow of drug (e.g., volume and/or flow rate) being ejected therefrom. As a result, the microstructures can create different drug release responses in different portions of an adjunct.

For example, in one exemplary embodiment, the adjunct can be formed of at least one fused bioabsorbable polymer and can have a lattice macrostructure having at least one drug contained therein. The lattice macrostructure can be formed of unit cells, and each unit cell can be configured to eject a predetermined amount of drug from the adjunct and the predetermined amount of the drug being a function of a compression profile of the respective unit cell. As such, drug delivery can therefore be controlled by the compression profiles of the unit cells.

The unit cells can have a variety of configurations. For example, in some embodiments, the unit cells are Schwarz-P structures. In one embodiment, the Schwarz-P structures are hollow. In certain embodiments, the lattice microstructure includes connecting structures that extend between and connect adjacent Schwarz-P structures to each other. In one embodiment, the connecting structures are in the form of hollow tubes. In such embodiments, the Schwarz-P structures can be in fluid communication with each other such that a continuous network of pathways are present or formed within the adjunct.

In some embodiments, the adjunct can include first unit cells having a first compression profile and second unit cells having a second compression profile that is different than the first compression profile. As such, different portions of the adjunct can therefore have different drug release rates. For example, the portions of the adjunct that are formed of the first unit cells can have a first release rate of drug that is a function of the first compression profile and the portions of the adjunct that are formed of the second unit cells can have a second release rate of drug that is a function of the second compression profile.

One or more of unit cells of an adjunct can have different compression zones. For example, in some embodiments, a unit cell can include two compression zones, in which the first compression zone has a first compressive strength and the second compression zone has a second compressive strength that is different than the first compressive strength. The first compression zone can be configured to compress from a first uncompressed height to a first compressed height. The second compression zone can be configured to compress from a second uncompressed height to a second compressed height that is different than the first compressed height. A person skilled in the art will appreciate that the compressive strength of the respective compression zone of a unit zone can depend at least upon the location of the unit cell within the adjunct (e.g., relative to an intended cut line of the adjunct) and/or the intended drug delivery site.

In some embodiments, the deformation properties of an adjunct can be controlled by sub-structures formed in one or more unit cells. For example, the sub-structures can be configured to change the deformation properties, deformation limits, bulk modulus, etc. of the unit cells relative to the intended staple line(s) and/or the intended cut line of the adjunct so as to create differing mechanical responses in different portions of the adjunct. As such, this can allow for a non-uniform pressure distribution against tissue that is stapled to the adjunct. Moreover, since drug is contained within one or more unit cells, this can create different drug release properties laterally relative to the intended cut line of the adjunct. The zones of healing from the cut line to the unrestrained portion of the tissue can require differing drug and doses to induce the proper healing. In one embodiment, unit cells can differ in size, release mechanism (e.g., bolus vs graduated release), and/or drug or drug combinations (e.g., the unit cells can differ laterally along the adjunct in a y-direction).

In one embodiment, the sub-structures can be configured to contact each other as the adjunct compresses. This resulting contact can either increase the bias (e.g., stiffness) of the adjunct, or alternatively, inhibit or stop any further compression or collapse of the adjunct. Alternatively, or in addition, the overall geometry of the unit cells can impact the deformation properties of the adjunct. For example, in one embodiment, one or more unit cells can have a variable wall thickness In another embodiment, one or more unit cells can have a thinner wall thickness and have an integral structure (e.g., a living hinge or like structure) that is configured to induce bending in a predefined location.

Figure 15:
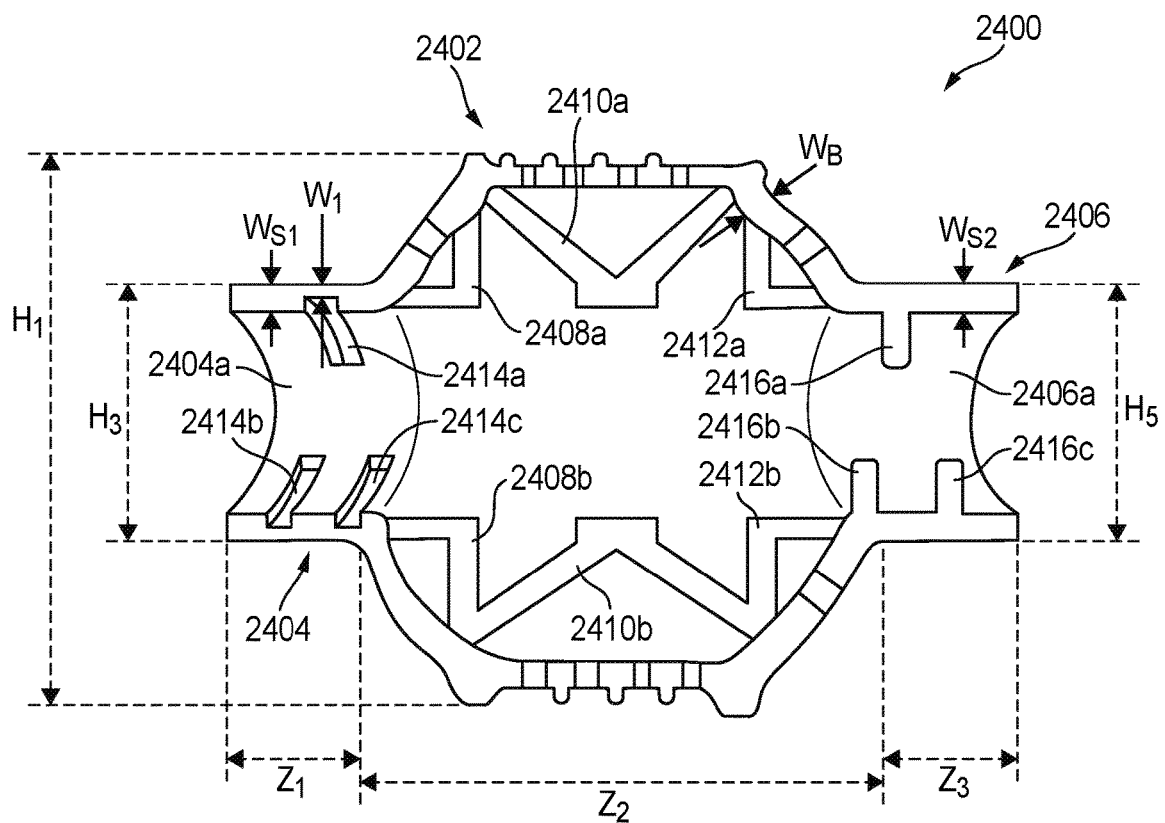
FIG. 15 is a cross-sectional view of a portion of another embodiment of adjunct, showing the adjunct in an uncompressed state.
Figure 16:
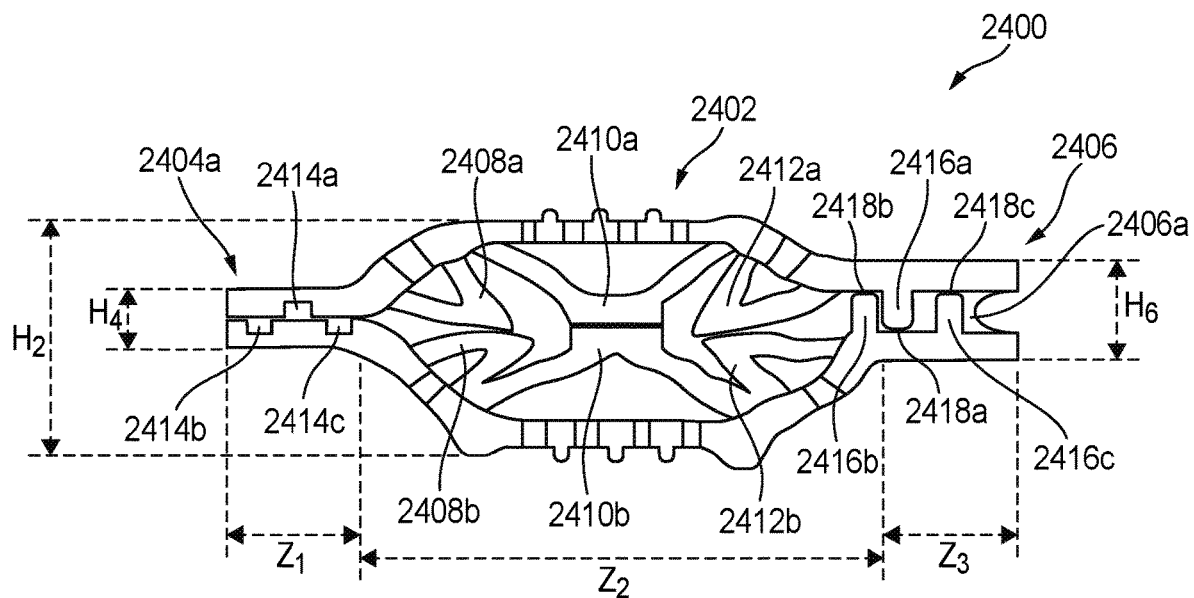
FIG. 16 is the adjunct of FIG. 15, showing the adjunct in a compressed state.

FIG. 15 and FIG. 16 illustrate an exemplary embodiment of a unit cell 2400 (e.g., microstructure) that can be configured to eject a predetermined amount of drug (not shown). While the unit cell 2400 can have a variety of configurations, in this illustrated embodiment, the unit cell 2400 is hollow and has a base structure 2402 with first and second side structures 2404, 2406. The first and second side structures 2404, 2406 extend outward from opposite sides of the base structure 2402. While the structural configurations of the base structure 2402 and the first and second side structures 2404, 2406 can vary, in this illustrated embodiment, the base structure 2402 has a generally spherical shape and the first and second side structures 2404, 2406 each have a generally cylindrical shape. Further, the unit cell 2400 can have a variable wall thickness, in which the base structure 2402 has a maximum wall thickness WB that is greater than the maximum wall thickness $W_{S1}$ of the first side structure 2404 and the maximum wall thickness $W_{S2}$ of the second side structure 2406.

As further shown, the unit cell 2400 includes sub-structures that are formed in different sections of the unit cell 2400. More specifically, the unit cell 2400 includes first sub-structures 2408a, 2408b, second sub-structures 2410a, 2410b, and third sub-structures 2412a, 2412b that are formed in the base structure 2402, fourth sub-structures 2414a, 2414b, 2414c that are formed in the first side structure 2404, and fifth sub-structures 2416a, 2416b, 2416c that are formed in second side structure 2406. These sub-structures are configured to effect different mechanical behaviors within the unit cell 2400 when the unit cell 2400 is being compressed (see FIG. 16). As a result, the unit cell 2400 has three different compression zones Z1, Z2, Z3, each having a different compressive strength. These three compression zones Z1, Z2, Z3 together define the compression profile of the unit cell 2400. In can be appreciated that the amount of compression experienced by the respective compression zones Z1, Z2, Z3 will therefore dictate the driving force applied to the drug retained therein. Accordingly, the compression profile can be used control the release rate of the drug from unit cell 2400.

The sub-structures can have a variety of configurations. In this illustrated embodiment, the first, second, and third sub-structures 2408a, 2408b, 2410a, 2410b, 2412a, 2412b are each internal stopping members, the fourth sub-structures 2414a, 2414b, 2414c are recesses that are defined within the wall 2404a of the first side structure 2404, and the fifth sub-structures 2416a, 2416b, 2416c are projections that partially extend inward from the wall 2406a of the second side structure 2406. The internal stopping members are configured to limit the amount of compression of the base structure when the unit cell is being compressed. In use, as shown in FIG. 16, the first internal stopping members 2408a, 2408b contact each other, the second internal stopping members 2410a, 2410b, and the third internal stopping members 2412a, 2412b contact each other, thereby increasing the stiffness of the base structure 2402 as it is compressed from an uncompressed height $H_1$ (FIG. 15) to a compressed height $H_2$. The recesses 2414a, 2414b, 2414c create weakened portions within the wall 2406a and therefore are configured to decrease the stiffness of the first side structure 2404. In use, as shown in FIG. 16, the first side structure 2404 fully compresses from an uncompressed height $H_3$ (FIG. 15) to a compressed height $H_4$. The projections 2416a, 2416b, 2416c within the second side structure 2406 form partial walls that are configured to limit the amount of compression of the second side structure 2406 when the unit cell 2400 is being compressed. In use, as shown in FIG. 16, the free ends 2418a, 2418b, 2418c of the projections 2416a, 2416b, 2416c come in contact with respective facing portions of the wall 2406a. As such, the projections 2416a, 2416b, 2416c thereby increase the stiffness of the second side structure 2406 as it is compressed from an uncompressed height $H_5$ (FIG. 15) to a compressed height $H_6$.

In certain embodiments, the adjuncts can be designed such that they possess rate dependent compressive properties. For example, an adjunct can include a series of interconnected fluid pockets (fluid filled) that are configured to transfer volume from one to another during compression, e.g., to thereby overcome or resist tissue flow. In one embodiment, two interconnected pockets exhibiting differing stiffness can transfer volume from the less stiff pocket to the more stiff pocket during tissue compression. This volume transfer could be used to prevent tissue from flowing away from a cutting element when the adjunct and tissue are being severed. In certain embodiments, a one-way valve between adjacent pockets can be configured to prevent backflow.

Figure 17:
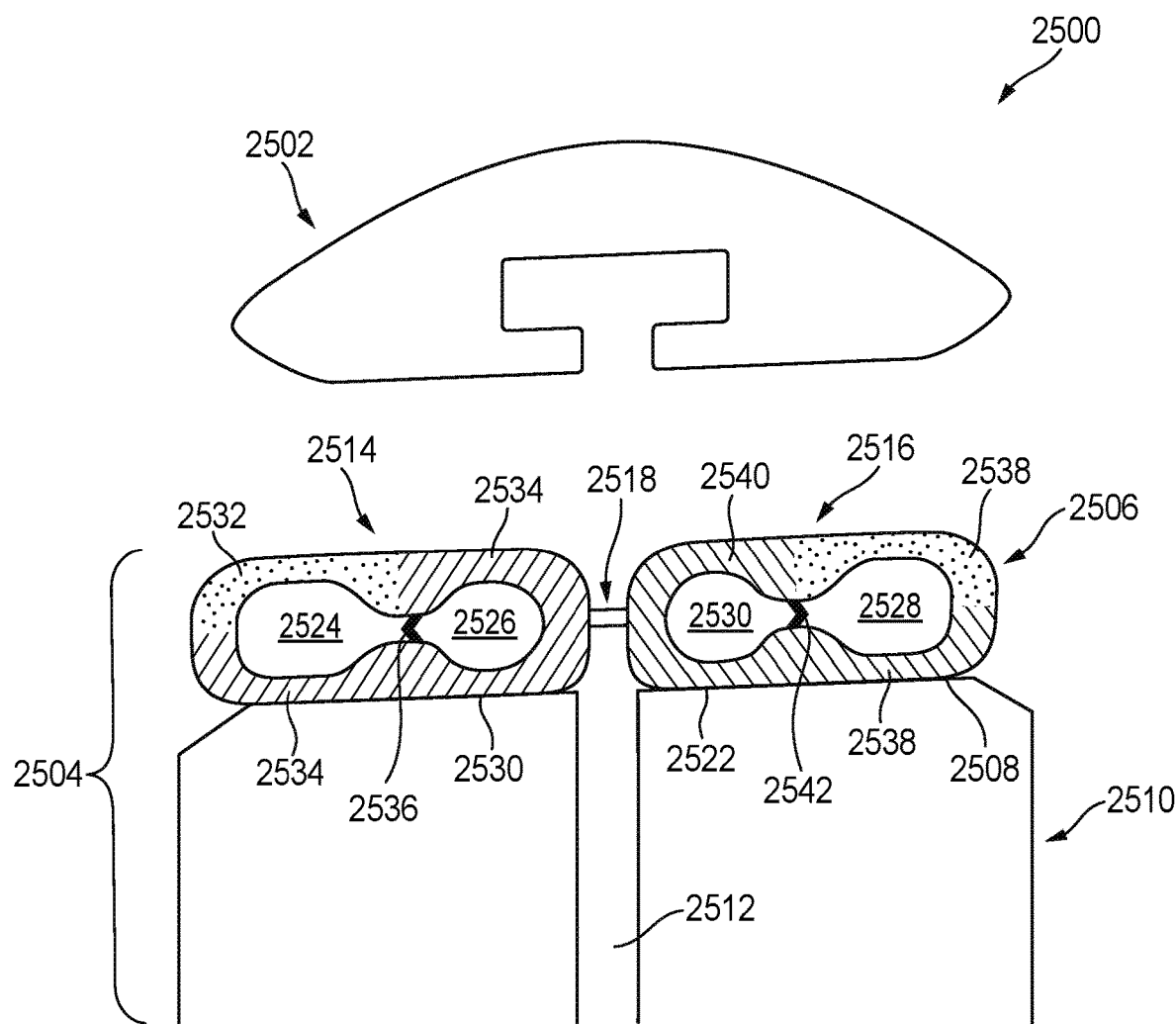
FIG. 17 is a cross-sectional front view of another embodiment of a surgical end effector having an anvil and a stapling assembly, the stapling assembly having another embodiment of an adjunct releasably retained on a staple cartridge, showing the surgical end effector in a closed positioned without tissue positioned between the anvil and the stapling assembly.

FIG. 17 illustrates another exemplary embodiment of a surgical end effector 2500 having an anvil 2502 and a stapling assembly 2504. The stapling assembly 2504 includes an adjunct 2506 releasably retained on a top or deck surface 2508 of a staple cartridge 2510 (e.g., the cartridge surface that faces the anvil). As shown, the cartridge 2510 has a slot 2512 that is defined within the cartridge 2510 and is configured to receive a cutting element (not illustrated). While not illustrated, the anvil 2502 is pivotally coupled to an elongate staple channel and the stapling assembly 2504 is positioned within and coupled to elongate staple channel.

The adjunct 2506 can have a variety of configurations. In this illustrated embodiment, the adjunct 2506 has a first longitudinal segment 2514 and an opposing, second longitudinal segment 2516 that are interconnected to each other via a connecting structure 2518 that extends therebetween. As shown in FIG. 17, the first longitudinal segment 2514 is positioned on a first side 2520 of the slot 2512, the second longitudinal segment 2516 is positioned on a second, opposing side 2522 of the slot 2512, and the connecting structure 2518 overlaps with the slot 2512.

The first longitudinal segment 2514 and the second longitudinal segment 2516 can have a variety of configurations. In this illustrated embodiment, the first longitudinal segment 2514 includes first and second interconnected pockets 2525, 2526 defined therein, and the second longitudinal segment 2516 includes third and fourth interconnected pockets 2528, 2530 defined therein. The first and second interconnected pockets 2525, 2526 are fluid filled and are configured to transfer volume(s) of the fluid between each other during compression of the adjunct 2506 (e.g., during clamping, stapling, and/or cutting and/or when the adjunct is in a tissue deployed state). As a result, fluid transfer between the first and second interconnected pockets 2525, 2526 can inhibit or resist tissue flow in undesirable directions (e.g., in a direction away from the slot 2512 and/or cutting element).

Similarly, the third and fourth interconnected pockets 2528, 2530 are fluid filled and are configured to transfer volume(s) of the fluid between each other during compression of the adjunct 2506 (e.g., during clamping, stapling, and/or cutting and/or when the adjunct is in a tissue deployed state). As a result, fluid transfer between third and fourth interconnected pockets 2528, 2530 can inhibit or resist tissue flow in undesirable directions (e.g., in a direction away from the slot 2512 and/or cutting element).

In certain embodiments, the first and second interconnected pockets 2525, 2526 can be configured to exhibit differing stiffness. For example, as shown in FIG. 17, the first interconnected pocket 2525 is bounded by a first wall 2532 formed of a first material (illustrated by stippling) and a second material (illustrated by hatching), whereas the second interconnected pocket 2526 is bounded by a second wall 2534 formed of only the second material (illustrated by hatching). In some embodiments, the first material is stiffer than the second material, whereas in other embodiments, the second material is stiffer the first material. In this illustrated embodiment, the second material is stiffer than the first material. Further, to prevent backflow, a one-way valve 2536 (e.g., a flapper valve, a duckbill valve, and the like) can be positioned between the first and second interconnected pockets. As shown, the one-way valve 2532 is configured to allow fluid to transfer from only the second interconnected pocket 2526 to the first interconnected pocket 2525.

Similarly, in certain embodiments, the third and fourth interconnected pockets 2528, 2530 can be configured to exhibit differing stiffness. For example, as shown in FIG. 17, the third interconnected pocket 2528 is bounded by a third wall 2538 formed of a first material (illustrated by stippling) and a second material (illustrated by hatching), whereas the fourth interconnected pocket 2530 is bounded by a fourth wall 2540 formed of only the second material (illustrated by hatching). In some embodiments, the first material is stiffer than the second material, whereas in other embodiments, the second material is stiffer the first material. In this illustrated embodiment, the second material is stiffer than the first material. Further, to prevent backflow, a one-way valve 2542 (e.g., a flapper valve, a duckbill valve, and the like) can be positioned between the first and second interconnected pockets. As shown, the one-way valve 2542 is configured to allow fluid to transfer from only the fourth interconnected pocket 2530 to the third interconnected pocket 2528.

The adjunct can be configured to exhibit rate dependent compressible properties that can be used as a mechanism for controlling tissue flow during compression. By way of example, FIG. 18 illustrates a surgical end effector 2600 having that is similar to the surgical end effector 2500 in FIG. 17 except for the differences described below.

Figure 18:
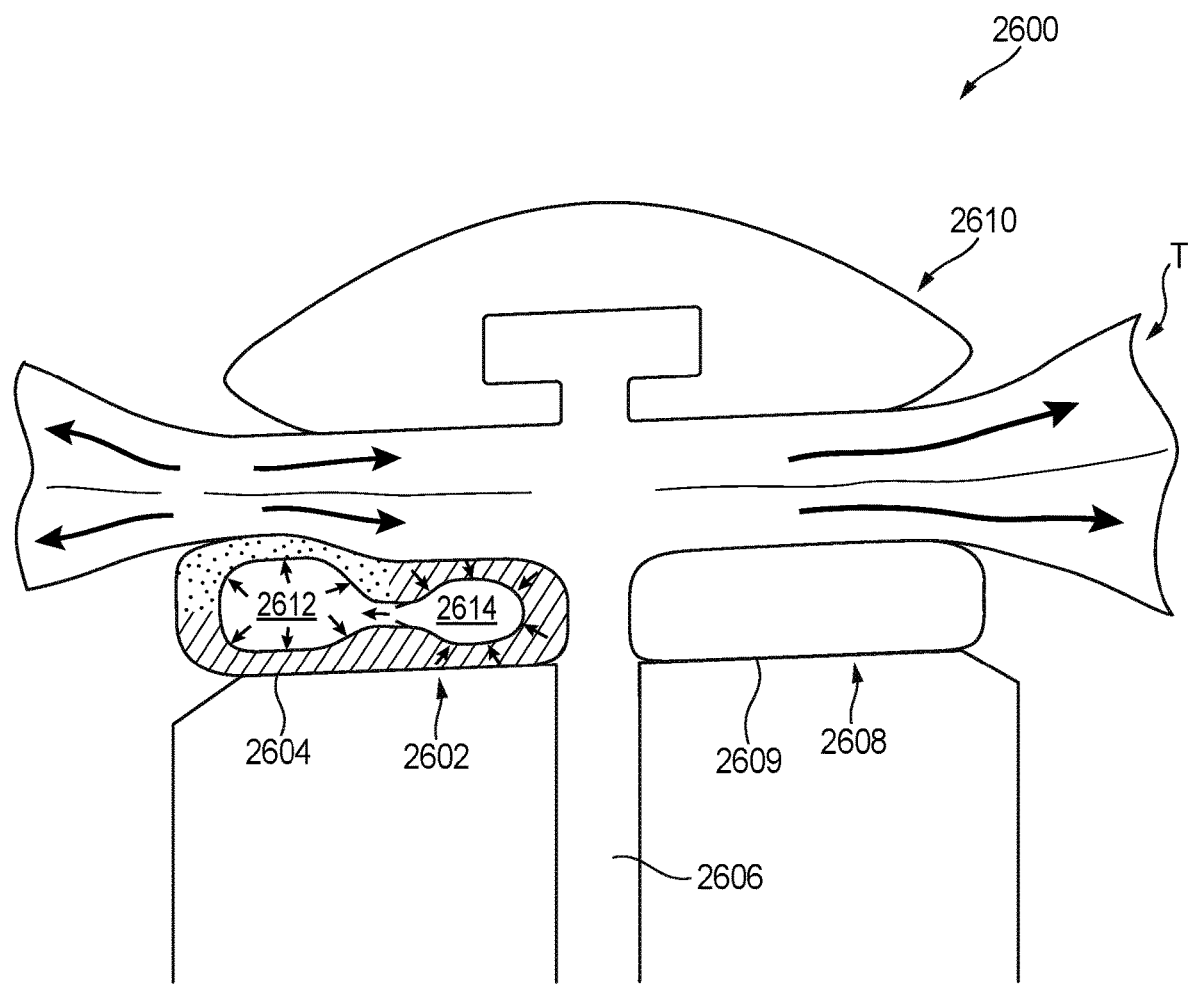
FIG. 18 is a cross-sectional front view of another embodiment of a surgical end effector having an anvil and a stapling assembly, the stapling assembly having an another embodiment of an adjunct releasably retained on a staple cartridge, showing the surgical end effector in a closed positioned without tissue positioned between the anvil and the stapling assembly.

As shown in FIG. 18, a first adjunct 2602 with rate dependent compressible properties is disposed on a first side 2604 of the slot 2606 and a second adjunct 2608 without rate dependent compressible properties is shown on the second, opposing side 2609 of the slot 2606. The first adjunct 2602 is structurally similar to the first longitudinal segment 2414 of the adjunct 2506 in FIG. 17, and therefore, common features are not described in detail herein. As shown, when tissue T is clamped between the anvil 2610 and the first adjunct 2602, the rate dependent compressible properties of the first adjunct 2602 minimize tissue flow away from the slot 2606. More specifically, upon compression, fluid transfer from the second interconnected pocket 2614 to the first interconnected pocket 2612 occurs thereby causing the first interconnected pocket 2612 to expand. As a result, tissue flow (depicted as dashed arrows) can be partially redirected back towards the slot 2606. By way of comparison, upon compression of the second adjunct 2608, as shown in FIG. 18, redirection of tissue flow (e.g., toward the slot 2606) does not otherwise occur.

A person skilled in the art will appreciate that the present invention has application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A compressible adjunct for use with a staple cartridge, the compressible adjunct comprising:
a non-fibrous adjunct material formed of at least one fused bioabsorbable polymer and configured to be releasably retained on a staple cartridge and configured to be delivered to tissue by deployment of staples in the cartridge, the adjunct material comprising a lattice macrostructure having at least one drug contained therein, the lattice macrostructure being formed of a plurality of unit cells, wherein each unit cell is configured to eject a predetermined amount of drug from the adjunct material and the predetermined amount of the drug being a function of a compression profile of the respective unit cell;
wherein the plurality of unit cells include first unit cells having a first compression profile and second unit cells having a second compression profile that is different than the first compression profile.

2. The adjunct of claim 1, wherein each unit cell comprises a plurality of compression zones.

3. The adjunct of claim 2, wherein the plurality of compression zones comprise a first compression zone having a first compressive strength and a second compression zone having a second compressive strength that is different than the first compressive strength.

4. The adjunct of claim 3, wherein the first compression zone is configured to compress from a first uncompressed height to a first compressed height, and wherein the second compression zone is configured to compress from a second uncompressed height to a second compressed height that is different than the first compressed height.

5. The adjunct of claim 1, wherein the plurality of unit cells comprise Schwarz-P structures.

6. The adjunct of claim 5, wherein the lattice macrostructure comprises a plurality of connecting structures that extend between and connect adjacent Schwarz-P structures to each other.

7. The adjunct of claim 1, wherein at least one unit cell of the plurality of unit cells has a variable wall thickness.

8. A compressible adjunct for use with a staple cartridge, the compressible adjunct comprising:
a non-fibrous adjunct material formed of at least one fused bioabsorbable polymer and configured to be releasably retained on a staple cartridge and configured to be delivered to tissue by deployment of staples in the cartridge, the adjunct material comprising a lattice macrostructure having at least one drug contained therein, the lattice macrostructure being formed of a plurality of unit cells, wherein each unit cell is configured to eject a predetermined amount of drug from the adjunct material and the predetermined amount of the drug being a function of a compression profile of the respective unit cell;
wherein each unit cell includes a plurality of sub-structures formed therein and configured to control the deformation behavior of the respective unit cell when the adjunct material is being compressed.

9. The adjunct of claim 8, wherein the plurality of sub-structures comprise first sub-structures and second sub-structures, wherein the first sub-structures are projections that extend inward from a wall of the unit cell and the second sub-structures are recesses formed in a wall of the unit cell.

10. The adjunct of claim 8, wherein the plurality of sub-structures comprise at least one internal stopping member.

11. A compressible adjunct for use with a staple cartridge, the compressible adjunct comprising:
a non-fibrous adjunct material formed of at least one fused bioabsorbable polymer and configured to be releasably retained on a staple cartridge and configured to be delivered to tissue by deployment of staples in the cartridge, the adjunct material comprising a lattice main structure having at least one drug contained therein, the lattice main structure comprising first sub-structures formed in at least one first portion of the lattice main structure and second sub-structures formed in at least one second portion of the lattice main structure, wherein the first sub-structures and the second sub-structures are configured to control a first release rate and a second release rate, respectively, of the at least one drug from the adjunct material when the adjunct material is compressed and in a tissue deployed state, the first release rate being different than the second release rate.

12. The adjunct of claim 11, wherein the first portion of the lattice main structure has a first wall thickness and the second portion of the lattice main structure has a second wall thickness that is different than the first wall thickness.

13. The adjunct of claim 11, wherein the first portion of the lattice main structure is configured to deform from a first undeformed state to a first deformed state.

14. The adjunct of claim 13, wherein the second portion of the lattice main structure is configured to deform from a second undeformed state to a second deformed state that is different than the first deformed state.

15. The adjunct of claim 11, wherein the first sub-structures comprises at least one of a first projection that extends inward from a wall of the lattice main structure and a first recess formed in a wall of the lattice main structure.

16. The adjunct of claim 11, wherein the second sub-structures comprises at least one of a second projection that extends inward from a wall of the lattice main structure and a second recess formed in a wall of the lattice main structure.

17. The adjunct of claim 11, wherein at least one of the first sub-structures and the second sub-structures comprise at least one internal stopping member.

18. The adjunct of claim 11, wherein the lattice main structure comprises a plurality of Schwarz-P structures.

19. The adjunct of claim 18, wherein the lattice main structure comprises a plurality of connecting structures that extend between and connect adjacent Schwarz-P structures to each other.

\* \* \* \* \*